(12) United States Patent
Bodor et al.

(10) Patent No.: US 8,702,684 B2
(45) Date of Patent: Apr. 22, 2014

(54) THERAPEUTIC HYBRID IMPLANTABLE DEVICES

(75) Inventors: Nicholas Bodor, Bal Harbour, FL (US);
Peter Buchwald, Weston, FL (US);
Christopher A. Fraker, Hollywood, FL (US); Jeffrey Hubbell, Morges (CH);
Luca Inverardi, Miami Beach, FL (US);
Norma Sue Kenyon, Miami, FL (US);
Paul Latta, Miami, FL (US); Antonello Pileggi, Aventura, FL (US); Cheryl Stabler Anderson, Coral Gables, FL (US); Fabio Grassi, Bellinzona (CH);
Camillo Ricordi, Miami, FL (US)

(73) Assignees: University of Miami, Miami, FL (US);
Converge Biotech Inc., Miami, FL (US)

( * ) Notice: Subject to any disclaimer, the term of this patent is extended or adjusted under 35 U.S.C. 154(b) by 766 days.

(21) Appl. No.: 12/524,918

(22) PCT Filed: Feb. 1, 2008

(86) PCT No.: PCT/US2008/001433

§ 371 (c)(1),
(2), (4) Date: Apr. 21, 2010

(87) PCT Pub. No.: WO2008/097498

PCT Pub. Date: Aug. 14, 2008

(65) Prior Publication Data

US 2010/0204683 A1     Aug. 12, 2010

Related U.S. Application Data

(60) Provisional application No. 60/899,302, filed on Feb. 2, 2007, provisional application No. 60/899,811, filed on Feb. 5, 2007.

(51) Int. Cl.
*A61K 9/22* (2006.01)
*A61M 31/00* (2006.01)

(52) U.S. Cl.
USPC .......................................... 604/891.1; 604/59

(58) Field of Classification Search
USPC .............. 604/890.1–892.1, 11, 16, 57, 59–64
See application file for complete search history.

(56) References Cited

U.S. PATENT DOCUMENTS

| 4,696,286 A | 9/1987 | Cochrum |
| 4,935,000 A * | 6/1990 | Dudek ............................ 600/36 |

(Continued)

FOREIGN PATENT DOCUMENTS

| EP | 0223763 | 5/1987 |
| JP | 7-100661 | 11/1995 |

(Continued)

OTHER PUBLICATIONS

Andreopoulos et al., "Delivery of basic fibroblast growth factor (bFGF) from photoresponsive hydrogel scaffolds," *Biomaterials*, 27(11):2468-2476 (2006).

(Continued)

*Primary Examiner* — Bhisma Mehta
*Assistant Examiner* — Bradley Osinski
(74) *Attorney, Agent, or Firm* — Ropes & Gray LLP; Karen Mangasarian; Wyan-Ching Mimi Lee

(57) ABSTRACT

A device (10) for receiving implanted biological material includes a mechanoprotective surface (16) defining an adjacent space, an assembly (26, 28) for locally delivering media to said space, and a pump or slow/sustained release reservoir structure (14) operatively coupled to the assembly. The device may comprise an additional plunger body for being disposed in said space. The implanted biological material may be encapsulated or non-encapsulated.

19 Claims, 34 Drawing Sheets

(56) References Cited

U.S. PATENT DOCUMENTS

| | | | |
|---|---|---|---|
| 5,324,518 | A | 6/1994 | Orth et al. |
| 5,554,148 | A | 9/1996 | Aebischer et al. |
| 5,855,616 | A * | 1/1999 | Fournier et al. ............ 623/23.64 |
| 5,952,168 | A * | 9/1999 | Wowk et al. ................... 435/1.3 |
| 6,630,154 | B1 | 10/2003 | Fraker |
| 7,892,222 | B2 * | 2/2011 | Vardi et al. ................. 604/891.1 |
| 2004/0195710 | A1 | 10/2004 | Hubbell |
| 2005/0244459 | A1 * | 11/2005 | DeWitt et al. ................. 424/426 |
| 2006/0024276 | A1 | 2/2006 | Ricordi |
| 2007/0264343 | A1 | 11/2007 | Bernstein |
| 2008/0020998 | A1 | 1/2008 | Majeed |

FOREIGN PATENT DOCUMENTS

| | | |
|---|---|---|
| JP | 2651516 | 5/1997 |
| RU | 2143867 | 1/2000 |
| WO | WO 00/35371 | 6/2000 |
| WO | WO 2006/020288 A2 | 2/2006 |

OTHER PUBLICATIONS

Backman et al., "The generalizability of training gains in dementia: Effects of an imagery-based mnemonic on face-name retention duration," *Psychologically and Aging*, 6(3):489-492 (1991).

Beck et al., "Islet Encapsulation: Strategies to enhance islet cell function," *Tissue Engineering*, 13(3):1-11 (2007).

Berglund et al., "Incorporation of intact elastin scaffolds in tissue-engineered collagen-based vascular grafts," *Tissue Engineering*, 10(9-10):1526-1535 (2004).

Chandy et al., "Evaluation of modified alginate-chitosan-polyethylene glycol microcapsules for cell encapsulation," *Artificial Organs*, 23(10):894-903 (1999).

Chang et al., "The in vivo delivery of heterologous proteins by microencapsulated recombinant cells," *Trends in Biotechnology*, 17(2):78-83 (1999).

Chen et al., "Current and future applications of immunological attenuation via pegylation of cells and tissue," *Biodrugs*, 15(12):833-847 (2001).

Chen et al., "Nano-fibrous poly(L-lactic acid) scaffolds with interconnected spherical macropores," *Biomaterials*, 25(11):2065-2073 (2004).

Contreras et al., "A novel approach to xenotransplantation combining surface engineering and genetic modification of isolated adult porcine islets," *Surgery*, 136(3):537-547 (2004).

Crooks et al., "Microencapsulation of mammalian cells in a HEMA-MMA copolymer: effects on capsule morphology and permeability," *Journal of Biomedical Materials Research*, 24(9):1241-1262 (1990).

Cruise et al., "A sensitivity study of the key parameters in the interfacial photopolymerization of poly(ethylene glycol) diacrylate upon porcine islets," *Biotechnology and Bioengineering*, 57(6):655-665 (1998).

Cruise et al., "In vitro and in vivo performance of porcine islets encapsulated in interfacially photopolymerized poly(ethylene glycol) diacrylate membranes," *Cell Transplant*, 8(3):293-306 (1999).

Dusseault et al., "Microencapsulation of living cells in semi-permeable membranes with covalently cross-linked layers," *Biomaterials*, 26(13): 1515-1522 (2005).

Ellis et al., "Poly(lactic-co-glycolic acid) hollow fibre membranes for use as a tissue engineering scaffold," *Biotechnology and Bioengineering*, 96(1):177-187 (2006).

Esch et al., "Dielectric properties of alginate beads and bound water relaxation studied by electrorotation," *Biopolymers*, 50(3):227-237 (1999).

Folstein et al., "'Mini-mental state'. A practical method for grading the cognitive state of patients for the clinician," *Journal of Psychiatric Research*, 12(3):189-198 (1975).

Fraker et al., "The use of multiparametric monitoring during islet cell isolation and culture: a potential tool for in-process corrections of critical physiological factors," *Cell Transplantation*, 13(5):497-502 (2004).

Fukuhira et al., "Biodegradable honeycomb-patterned film composed of poly(lactic acid) and dioleoylphosphatidylethanolamine," *Biomaterials*, 27(9):1797-1802 (2006).

Geutjes et al., "From molecules to matrix: construction and evaluation of molecularly defined bioscaffolds," *Advances in Experimental Medicine and Biology*, 585:279-295 (2006).

Grant et al., "Biological interactions between polysaccharides and divalent cations: the egg-box model," *FEBS Letters*, 32(1):195-198 (1973).

Hada et al., "Covalent crosslinking of von Willebrand factor to fibrin," *Blood*, 68(1):95-101 (1986).

Hill et al., "Immunoisolation of adult porcine islets for the treatment of diabetes mellitus. The use of photopolymerizable polyethylene glycol in the conformal coating of mass-isolated porcine islets," *Annals of the New York Academy of Sciences*, 831:332-343 (1997).

Iwata et al., "Agarose for a bioartificial pancreas," *Journal of Biomedical Materials Research*, 26(7):967-977 (1992).

Iwata et al., "Evaluation of microencapsulated islets in agarose gel as bioartificial pancreas by studies of hormone secretion in culture and by xenotransplantation," *Diabetes*, 38(Suppl. 1):224-225 (1989).

Jain et al., "Retrievable, replaceable, macroencapsulated pancreatic islet xenografts. Long-term engraftment without immunosuppression," *Transplantation*, 59(3):319-324 (1995).

Juang et al., "Beneficial effects of hyperbaric oxygen therapy on islet transplantation," *Cell Transplantation*, 11:95-101 (2002).

Kang et al., "The use of poly(lactic-co-glycolic acid) microspheres as injectable cell carriers for cartilage regeneration in rabbit knees," *Journal of Biomaterials Science*, 17(8):925-939 (2006).

Kim et al., "Synthesis and characterization of injectable poly(N-isopropylacrylamideco-acrylic acid) hydrogels with proteolytically degradable cross-links," *Biomacromolecules*, 4(5):1214-1223 (2003).

Krol et al., "Multilayer nanoencapsulation. New approach for immune protection of human pancreatic islets," *Nano Letters*, 6(9):1933-1939 (2006).

Kwon et al., "Photo-iniferter-based thermoresponsive block copolymers composed of poly(ethylene glycol) and poly(N-isopropylacrylamide) and chondrocyte immobilization," *Biomaterials*, 27(7):986-995 (2006).

Lanza et al., "A simple method for transplanting discordant islets into rats using alginate gel spheres," *Transplantation*, 59(10):1485-1487 (1995).

Leach et al, "Crosslinked alpha-elastin biomaterials: towards a processable elastin mimetic scaffold," *Acta Biomaterialia*, 1(2):155-164 (2005).

Lee et al., "Collagen mimetic peptide-conjugated photopolymerizable PEG hydrogel," *Biomaterials*, 27(30):5268-5276 (2006).

Lee et al., "Optimization of monomethoxy-polyethylene glycol grafting on the pancreatic islet capsules," *Journal of Biomedical Materials Research*, 62(3):372-377 (2002).

Lewinska et al., "Influence of process conditions during impulsed electrostatic droplet formation on size distribution of hydrogel beads," *Artificial Cells, Blood Substitutes, and Immobilization Biotechnology*, 32(1):41-53 (2004).

Li et al., "Chitosan-alginate hybrid scaffolds for bone tissue engineering," *Biomaterials*, 26(18):3919-3928 (2005).

Li et al., "Transfer of apatite coating from porogens to scaffolds: uniform apatite coating within porous poly(DL-lactic-co-glycolic acid) scaffold in vitro," *Journal of Biomedical Materials Research*, 80(1):226-233 (2007).

Lu et al., "Cell encapsulation with alginate and alpha-phenoxycinnamylideneacetylated poly(allylamine)," *Biotechnology and Bioengineering*, 70(5):479-483 (2000).

Lu et al., "Novel porous aortic elastin and collagen scaffolds for tissue engineering," *Biomaterials*, 25(22):5227-5237 (2004).

Ma et al., "Potential of nanofiber matrix as tissue-engineering scaffolds," *Tissue Engineering*, 11(1-2):101-109 (2005).

Martinsen et al., "Alginate as immobilization material: I. Correlation between chemical and physical properties of alginate gel beads," *Biotechnology and Bioengineering*, 33(1):79-89 (1989).

(56) References Cited

OTHER PUBLICATIONS

Minquez-Castellanos et al., "Carotid body autotransplantation in Parkinson disease: a clinical and positron emission tomography study," *The Journal of Neurology, Neurosurgery, and Psychiatry*, 78:825-831 (2007).

Miura et al., "Encapsulation of islets with ultra-thin polyion complex membrane through poly(ethylene glycol)-phospholipids anchored to cell membrane," *Biomaterials* 27(34):5828-5835 (2006).

Orban et al., "Crosslinking of collagen gels by transglutaminase," *Journal of Biomedical Materials Research*, 68(4):756-762 (2004).

Panza et al., "Treatment of rat pancreatic islets with reactive PEG," *Biomaterials*, 21:1155-1164 (2000).

Puviani et al., "Morphological and functional evaluation of isolated rat hepatocytes in three dimensional culture systems," *International Journal of Artificial Organs*, 22(11):778-785 (1999).

Ramachandran et al., "Peptide-based viscoelastic matrices for drug delivery and tissue repair," *Biodrugs*, 20(5):263-269 (2006).

Ratcliffe, "Tissue engineering of vascular grafts," *Matrix Biology*,19(4):353-357 (2000).

Rinsch et al., "Delivery of erythropoietin by encapsulated myoblasts in a genetic model of severe anemia," *Kidney International*, 62(4):1395-1401 (2002).

Sefton et al., "Making microencapsulation work: conformal coating, immobilization gels and in vivo performance," *Journal of Controlled Release*, 65(1-2):173-186 (2000).

Shoichet et al., "Stability of hydrogels used in cell encapsulation: An in vitro comparison of alginate and agarose," *Biotechnology and Bioengineering*, 50(4):374-381 (1996).

Sun et al., "Microencapsulation of pancreatic islet cells: a bioartificial endocrine pancreas," *Methods in Enzymology*, 137:575-580 (1988).

Sun et al., "Use of ultrathin shell microcapsules of hepatocytes in bioartificial liver-assist device," *Tissue Engineering*, 9(Suppl 1):S65-S75 (2003).

Sun et al., "Microencapsulation of Living Cells—A Long-Term Delivery System," *Journal of Controlled Release*, 2:137-141 (1985).

Tun et al., "A newly developed three-layer agarose microcapsule for a promising biohybrid artificial pancreas: rat to mouse xenotransplantation," *Cell Transplantation*, 5(Suppl. 1):S59-63 (1996).

Watanabe et al., "Stereocomplex formation by enantiomeric poly(lactic acid) graft-type phospholipid polymers for tissue engineering," *Biomacromolecules*, 3(5):1109-1114 (2002).

Xie et al., "Cytoprotection of PEG-modified adult porcine pancreatic islets for improved xenotransplantation," *Biomaterials*, 26(4):403-412 (2005).

Yamaoka et al., "Cartilage tissue engineering using human auricular chondrocytes embedded in different hydrogel materials," *Journal of Biomedical Materials Research*, 78(1):1-11 (2006).

Yang et al., "Comparative studies of in vitro and in vivo function of three different shaped bioartificial pancreases made of agarose hydrogel," *Biomaterials*, 15(2):113-120 (1994).

Zheng et al., "Favorably tipping the balance between cytopathic and regulatory T cells to create transplantation tolerance," *Immunity*, 19(4):503-514 (2003).

Zmora et al., "Tailoring the pore architecture in 3-D alginate scaffolds by controlling the freezing regime during fabrication," *Biomaterials*, 23(20):4087-4094 (2002).

\* cited by examiner

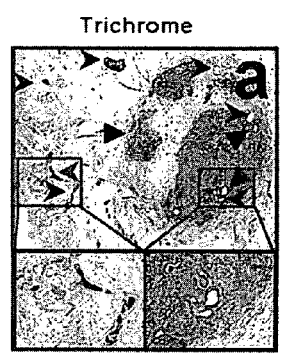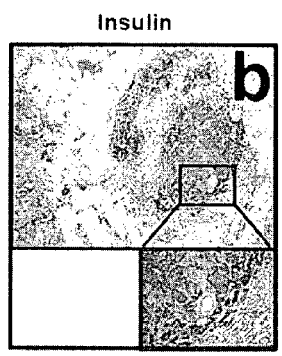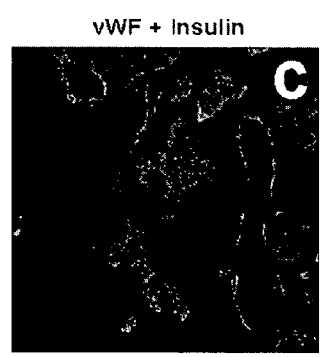
*FIG. 16a*   *FIG. 16b*   *FIG. 16c*

| TABLE 1 | | |
|---|---|---|
| Group | n | Graft Survival (Days) |
| Control | 3 | 9, 12, 15 |
| Sirolimus+Tacrolimus | 3 | >80 x 3 |

FIG. 20

THERAPEUTIC HYBRID IMPLANTABLE DEVICES

This application is a national stage application under 35 U.S.C. §371 of International Application PCT/US2008/001433, filed on Feb. 1, 2008, which claims the benefit of U.S. Provisional Application 60/899,302, filed on Feb. 2, 2007 and which claims the benefit of U.S. Provisional Application 60/899,811, filed on Feb. 5, 2007. The disclosure of PCT/US2008/001433 is hereby incorporated by reference in its entirety.

BACKGROUND OF THE INVENTION

Cell replacement therapy is a promising potential treatment option for a wide variety of diseases. Many clinical conditions and disease states result from the lack of factor(s) produced by living cells or tissues, including, for example, diabetes, in which insulin production is inadequate; Parkinson's disease, in which dopamine production is decreased; and anemia, in which erythropoietin is deficient. Such conditions or diseases may be treated by cell/tissue implants that produce the missing or deficient factor(s).

However, many challenges remain in the field of cell replacement therapy. The viability and functionality of transplanted cells is compromised by, for example, lack of mechanical protection, lack of necessary factors, e.g. by inadequate vascularization or by inability of the vascular system to reach parts of the transplant, and anti-transplant host immune activity. Thus, there is a need for methods and devices that optimize the viability and functionality of implanted cells.

PCT Application No. PCT/MX99/00039, published as PCT Publication WO 00/35371, the entire disclosure of which is incorporated herein by this reference, discloses a device for xenotransplantation of islet-Sertoli cell mixtures. This is a device in which new capillaries are allowed to grow through a cylindrical, perforated metal mesh, which contains a non-completely occluded plastic (e.g., Teflon® or Gore-Tex®) plunger. An open space of approximately 1 mm is defined between the plunger and the mesh to allow for new capillaries to grow through the external wall of the device, providing a vascular bed between the plunger and the mesh. After some time (4-8 weeks), the plunger is removed and the selected cells for transplant are deposited in its stead.

The availability of a capillary bed in close proximity to the implanted cells, in an exemplary case islet cell clusters, is disclosed as promoting engraftment of the cellular transplant. Furthermore, the presence of the co-transplanted Sertoli cells is thought to confer immunoprotection/immunomodulation within the device. Sertoli cells are derived from the testis and express FasL (Fas ligand). These cells are thought to confer local immunoprotection and in the case of the testis microenvironment, to allow for prolonged survival of other cell types transplanted into the testis. Intratesticular transplantation of cells such as islets, or co-transplantation of islets with Sertoli cells has been attempted for the past two decades, with the objective of conferring immunoprotection from the immune-attack of the transplanted cells by the recipient immune system.

While the above-described approach has potential advantages, according to the system design, the implanted cells can still be recognized by the recipient's immune system as non-self, foreign live biologic tissues, and will thus be subject to an immune response that, in the case of allogeneic and especially xenogeneic or heterologous grafts, will be particularly strong. See, for example, FIG. 20. The result is that the implanted cells will be attacked as foreign tissues and even co-transplantation of Sertoli cells alone may not be sufficient to protect the therapeutic cells type. Thus, powerful systemic immunosuppression of the patient may nevertheless be required, especially in the case of transplantation between species such as pig to human. Moreover, a potential disadvantage of the above-proposed cylindrical device is that the deposited cylindrical column of cells will be too thick for the nutrients from the new capillaries to reach the more inwardly disposed cells, before the full thickness of the cellular implant will be fully vascularized by the peripheral capillary bed, so that these cells may not thrive and/or only a small portion of the implanted cells may survive until adequate re-vascularization occurs.

The host immune response may be prevented or minimized by encapsulation of the implanted cells with biocompatible, semi-permeable, immune-protective material or other materials by methods known in the art. The permeability of such materials are selected to allow cells to exchange oxygen, nutrients, and other small molecules with the host environment, but that diminish or prevent attack of the cells by large host immune system components such as immune cells and antibodies. In this regard, a variety of cell encapsulation methods are known in the art. Encapsulated cells may take the form of, for example, a macrostructure scaffold, a microcapsule, a nanocapsule, linked extruded capsules, or any combination thereof. These forms differ in many variables, including size, volume of cells contained, and strength and diffusion characteristics.

Encapsulated systems alone, however, do not provide the implanted cells with long-term mechanical or immune protection. Over time, and with exposure to peristalsis, compression, and pressure, among other physical insults, the capsules can break, degrade, or tear, exposing the implanted cells to physical damage as well as damage from the host immune system. In addition, it is difficult to sustain living cells within biocompatible materials for long periods of time. Cells that are not in proximity to oxygen and other growth factors and nutrients that are continuously delivered to vascularized tissue, such as those in central portions of the biological material, tend to become necrotic and to poison healthier cells in the periphery of the capsule.

Accordingly, it is an object of the present invention to avoid the requirement for long term systemic immunosuppression of recipients of cellular transplants, which currently limits the applicability of such procedures to the most severe cases of disease state for which the cellular therapy is indicated (e.g., hypoglycemia unawareness and labile diabetes in the case of insulin dependent diabetes).

It is also an object of the invention to provide an assembly that facilitates the addition of factors to favor engraftment and function of transplanted cells and tissues, before, during, and after re-vascularization of a biological material implant.

It is a further object of the invention to provide a receptacle for implanted biological material that favors cellular survival by providing mechanical support while (a) maximizing exposure of the transplant to new capillaries growing within and/or around the device (for example, by delivery of VEGF or VEGF pathway agonists or the use of degradable, angiogenic materials); and (b) locally delivering substances that can promote not only growth of new capillaries but also protect/enhance the implanted biological material, e.g. cells/tissues and/or products thereof (such as, e.g., anti-inflammatory, antiapoptotic products and/or growth factors such as corticosteroids (e.g., prednisolone, dexamethasone, loteprednol etabonate, flucinolone acetonide, etc.), IGF-I, IGF-II, HGF, GLP-1, Exendin-4, INGAP, lysophylline, pentoxyfilline;

COX-2 inhibitors; interleukin-1 receptor antagonist peptide (IRAP), interleukin-10 (IL-10), alpha 1-antitrypsin (AAT), TGF-beta; antibodies to IL-1, interferon-gamma, and TNF-alpha; anti-tissue factor, complement inhibitors, oxygen generating, releasing (such as encapsulated peroxides), or transport-enhancing (such as perfluorocarbon PFC) products; as well as endothelial progenitor cells, stem cells, regulatory T cells $T_{reg}$, or any others known to those skilled in the art, which may optionally or additionally be encapsulated.

SUMMARY OF THE INVENTION

To achieve the foregoing and other objects, the invention provides a hybrid device that enables cellular therapy to be performed upon implantation into a subject in need thereof. Hybrid devices comprise (a) a biological material, such as a composition comprising one or more desired cell or tissue types or a product of such cells or tissues, and/or optionally other biocompatible materials; coupled with (b) a delivery system (such as, e.g., a pump or a slow/sustained release reservoir), either external, externally accessible or internal, to locally deliver one or more agents, such as immunosuppressive/immunoregulatory molecules and/or selected nutrients and growth factors that promote survival of the transplanted cells and preferably regeneration and expansion thereof. As will be appreciated, the local delivery of selected nutrients, factors, cytokines, drugs and the like will facilitate establishment, maintenance, and long term survival and function of biological material, e.g. transplanted cells, while minimizing the side effects of recipient immunosuppression.

The invention addresses the problem of transplant rejection by optionally providing localized immunosuppression/immunoregulation, which will allow for localized delivery of therapeutic levels of immunosuppressive/immunoregulatory substances, while avoiding the requirement for long term systemic immunosuppression of the recipient patient. The invention also addresses these problems by providing local delivery of factors beneficial to the biological material, such as, e.g., those that favor cell engraftment, growth, and function.

In certain embodiments, the biological material is a composition comprising one or more select cell types or tissues. In certain embodiments, the biological material is a composition consisting essentially of one or more select cell types or tissues. In certain embodiments, the biological material is a composition consisting of one or more select cell types or tissues. In certain of these embodiments, the invention further addresses the problem of rejection of the cellular transplant by optionally encapsulating the cells within a biocompatible material, e.g., a matrix biomaterial, providing protection from mechanical stress and from the host immune system. Encapsulation of the cells may reduce or preferably minimize the need for even local delivery of immunosuppressive/immunoregulatory substances upon implant. The encapsulated cells are further protected by the mechanical support provided by the hybrid device. In some embodiments, the biological material comprises a mixture of encapsulated and non-encapsulated cells/tissue and/or products thereof.

Thus, in an exemplary embodiment, the invention provides a hybrid device that comprises a microenvironment favorable to cell and/or tissue survival and function, e.g. by providing a vascularized bed for the implanted biological material; and a delivery system for local delivery of one or more nutrients, factors, cytokines, and immunosuppressive/immunoregulatory molecules directly or indirectly to the implanted biological material contained in the device. The delivery system such as a pump or other reservoir (including slow/sustained release cartridges, coatings, encapsulations, micro- or nanospheres, etc.) may be external or externally accessible, which would generally be preferred for ease of loading of different media cartridges; or internal, e.g. subcutaneous, preferably with a loading port and remotely controllable delivery-rate device.

Loading of selected agents, preferably by a replaceable/disposable cartridge in an externally accessible pump or other delivery system selected from those mentioned in the previous paragraph, can be tailored to the different requirements of the implanted cellular environment at different times. In certain embodiments, some or all of the implanted biological material (e.g. a composition comprising one or more types of cells, tissues, or cell products, or a combination thereof) is encapsulated in a biocompatible, and preferably immune-protective, material. The encapsulated cells are protected from physical trauma by the mechanical support provided by the hybrid device.

In certain embodiments, the implanted cells (i.e., those implanted to deliver a therapeutic effect, e.g. a therapeutic factor, to the patient) may be one or more of autologous, heterologous, syngeneic, allogeneic, or xenogeneic pancreatic islets, alone or in combination with other cell types (e.g., Sertoli cells, mesenchymal and bone marrow derived cells, endothelial progenitor cells, stem cells, regulatory T cells $T_{reg}$, etc., each referred to generically as implant "helper cells") that provide growth factors and/or other beneficial agents for establishment, maintenance or expansion of the implanted cells, or otherwise to help the implanted cells deliver the therapeutic effect.

Besides pancreatic islets, which are considered one preferred cell/tissue type for regulating sugar and energy metabolism, and for treating diabetes, the hybrid devices of the invention and methods involving those devices may also be applied to other tissue and cell therapy model systems. Tissues and cells for implantation may deliver a therapeutic benefit, e.g. by expressing a therapeutic factor in vivo. Examples of such tissues and cells include, but are not limited to, cells that produce: dopamine to treat Parkinson's disease (Minquez-Castellanos et al., *J Neurol Neurosurg Psychiatry* in press (2007)); growth hormone to treat dwarfism (Chang et al., *Trends Biotechnol* 17:78-83 (1999)); factor VIII and factor IX (Chang et al., *Trends Biotechnol* 17, 78-83 (1999)) to treat hemophilia; and erythropoietin to treat anemia (Rinsch et al., *Kidney Intern* 62:1395-1401 (2002)). Many more beneficial cell produced factors or cellular/tissue activities may be imagined. The implanted tissues or cells may express and/or deliver more than one therapeutic factor, or may comprise two or more cell types delivering one or more therapeutic factors. The implanted tissues or cells may also or alternatively express and/or deliver an agonist, analog, derivative, chimera, fusion, or fragment of a therapeutic factor to deliver a therapeutic effect.

The implanted tissues or cells may also or alternatively deliver a therapeutic effect without secreting a diffusible factor, e.g. by providing an enzymatic activity that, for example, converts a substrate into a product having a beneficial effect, and/or metabolizing, sequestering, or absorbing a detrimental substance. The implanted tissues or cells may deliver a therapeutic effect through a biological material-linked factor, such as a cell surface-linked factor.

The tissues or cells may naturally deliver a therapeutic effect, without genetic modifications, or may be genetically engineered to do so. For example, the biological material of the invention may comprise cells transfected with expression vectors that express one or more therapeutic and/or helper cell factors. In another embodiment, the biological material of the invention may consist essentially of cells transfected with expression vectors that express one or more therapeutic and/or helper cell factors. In another embodiment, the biological material of the invention may consist of cells transfected with expression vectors that express one or more therapeutic and/or helper cell factors. Such expression may be in a constitutive or in a regulated manner, e.g., in response to biological modulators in the bloodstream or tissues to which the hybrid device is exposed.

In some embodiments, the biological material is non-cellular. Such non-cellular biological material may be encapsulated or non-encapsulated, as described below.

In some embodiments, prior to implant, some or all of the biological material can be encapsulated with a biocompatible material to improve viability and to provide protection from the host environment. As well as providing structural integrity and mechanical strength, such encapsulation can further protect the implanted biological material, e.g. cells/tissue or products thereof, from the immune response of the host. Encapsulated cells are embodied in many different forms, such as, for example, a macrostructure scaffold, a microcapsule, a linked extruded capsule, or a nanocapsule. These forms differ in many variables, including size, volume of cells contained, and strength and diffusion characteristics. The particular set of variables may be selected by the skilled practitioner in consideration of the device, the cell type(s), the implant location and the therapeutic factor or factors being delivered, in view of the particular patient's condition and needs.

Preferably, cells are encapsulated so as to have permeability characteristics that allow exchange of nutrients and cellular by-products and release of therapeutic factors, but that may also preclude host immune effector molecules from entering the capsules.

Thus, the invention may be embodied in a device, which may be vascularized, for receiving implanted biological material, which may be encapsulated, comprising: a surface defining and mechanically shielding an adjacent space, such as an inner space; an assembly for selectively delivering at least one of immunosuppressive and/or growth factor media to said space; and a pump or a reservoir for such media, operatively coupled to said assembly. The device may be of any shape, including cylindrical or non-cylindrical shapes, or matrices or assemblies of cylindrical or non-cylindrical shapes. The shape of the device may vary based on the biological material to be implanted, the intended therapeutic effect, and/or the location of the implant, for example. The skilled practitioner can assess the shape(s) preferred for the intended application(s).

In certain embodiments, the device is similar in shape to the cylindrical device described in PCT Application No. PCT/MX99/00039 (published as PCT Publication WO 00/35371), in which new capillaries are allowed to grow through a mesh.

In certain embodiments, the device is similar to the flask-shaped device described in U.S. patent application Ser. No. 11/185,011 (published as U.S. Patent Publication No. US 2006/0024276), in which new capillaries are allowed to grow through a mesh. In this embodiment, a fluid manifold assembly is attached to one or more distribution conduits (a "sprinkler system") that provide media locally to the device content.

In certain embodiments, the device is a cage-like device, which may be cylindrical or non-cylindrical, in which new capillaries are allowed to grow through a mesh. In this embodiment, one or more distribution conduits provide media locally to the device content.

In certain embodiments, the device comprises an outer coil-shaped element non-completely enclosing an adjacent, e.g. inner, space. The open nature of the coil shape provides greater surface area to receive the transplanted cells. Further, the coil shape allows for greater diffusion of factors secreted by the transplanted cells. In this embodiment, the coil comprises the distribution conduit. One or more additional distribution conduits within the space defined by the coil may also provide media locally to the device content.

In certain embodiments, the device may comprise an outer coin-shaped frame, made of, e.g., a biocompatible plastic material such as Teflon® or GoreTex®, non-completely enclosing an adjacent, e.g. inner, space that can be vascularized after implant. In this embodiment, one or more distribution conduits provide media locally to the device content.

In certain embodiments, the device may comprise a mesh "sponge" element that allows for revascularization of the device content by recipient capillaries that can pass through the mesh. The sponge element may be non-completely enclosed by a shape, e.g. a disk, which may be made of a biocompatible plastic material such as Teflon® or GoreTex®, with rounded edges to eliminate sharp edges in the implant. In this embodiment, one or more distribution conduits provide media locally to the device content.

In any of the above embodiments, the device may contain a non-completely occluding plunger that is implanted with the device. After a period of time that allows for adequate vascularization of the area in and around the device, the plunger may be removed, and the space formerly occupied by the plunger may be filled with the biological material to be transplanted.

In any of the above embodiments, the device may include a delivery system that facilitates delivery of, for example, drugs and nutrients/growth factors to facilitate the establishment, maintenance and long term survival and function of biological material, e.g. transplanted cells. Such a delivery system may comprise, for example, a pump/reservoir, a port, a fluid or slow/sustained release assembly that may be a manifold assembly, and one or more distribution conduits that provide media locally to the device content. Such a delivery system may also comprise, for example, slow-release coatings, slow-release (optionally refillable) cartridges, or slow-release micro- or nanospheres. Slow/sustained release compositions and formulations are known in the art (see, e.g., U.S. Patent Publication Nos. 2007/0264343 and 2008/0020998).

In any of the above embodiments, the adjacent space for receiving biological materials may comprise a biocompatible material such as PET (or, for example, other mesh materials), which may be biodegradable. Before implantation, the biocompatible material may be seeded with the biological materials to be transplanted.

In any of the above embodiments, the factors delivered to the transplanted biological material through the local hybrid device delivery system may be formulated or encapsulated to provide delivery of said factors with slow/sustained release characteristics. In certain embodiments, continuous local delivery of media containing said factors to the transplanted cells may be replaced by administration of a less frequent bolus of said factors.

In any of the above embodiments, the factors to be administered may be modified, e.g., through PEGylation or inclusion of chemically or enzymatically labile moieties, such that said factors are metabolized readily upon leaving the space defined by the device. This may help to minimize unwanted systemic effects caused by the factors.

In any of the above embodiments, the device may further comprise a tether to facilitate manipulation and/or retrieval of the device from a patient.

In any of the above embodiments, the biological material may be implanted in a one-step or a two-step procedure, as described below.

The invention may also be embodied in a method for implanting biological material in a patient, comprising: providing a device for receiving biological material, said device including a mechanoprotective surface defining an adjacent, e.g. inner, space and a system for local delivery of media.

In a preferred embodiment, the invention may be embodied in a method for implanting biological material in a patient in a two-step procedure, comprising: (1) implanting a device for receiving biological material at a selected location within the patient, said device including a mechanoprotective surface defining an adjacent, e.g. inner, space; a plunger occupying a part of the adjacent space of the device; and an assembly for selectively delivering at least one of immunosuppressive and/or growth factor media to said adjacent space and a pump or a reservoir for such media, operatively coupled to said assembly; and allowing tissue ingrowth into said adjacent space; (2) removing the plunger and disposing a biological material comprising, for example, a selected tissue/cell product within the adjacent space vacated by the plunger, and selectively delivering at least one of an immunosuppressive and/or growth factor media to said adjacent space.

Alternatively, the invention may be embodied in a method for implanting biological material in a patient in a one-step procedure, comprising: implanting a device for receiving biological material at a selected location within the patient, the device including a mechanoprotective surface defining an adjacent space and an assembly for selectively delivering at least one of immunosuppressive and/or growth factor media to said adjacent space and a pump or a reservoir for such media, operatively coupled to the assembly, wherein the biological material to be deposited is pre-loaded into the device.

In some embodiments, such as those in which the device is cylindrical in shape, the invention may be embodied in a method for implanting the device in a two-step or one-step procedure as described above, such that it is not placed in contact with the wall of a lumen. In some embodiments, such as those in which the device is cylindrical in shape, the invention may be embodied in a method for implanting the device in a two-step or one-step procedure as described above, such that immunomodulatory/immunosuppressive agents are not delivered to the implanted biological material.

In certain embodiments, the implant location may be, for example, intraomental (in an omental pouch), subcutaneous, or intraperitoneal. In such cases, the output of the device may be into the portal system. In certain embodiments, the biological material comprises a cell/tissue or product thereof providing therapeutic benefit to the patient when implanted.

The invention may also be embodied in a method for implanting biological material in a patient, wherein prior to disposing the biological material within the space defined by the device, the biological material is encapsulated to provide a means to distribute, give structural integrity, and/or immunoprotect the cells. In certain embodiments, the biological material comprises a cell/tissue or product thereof providing therapeutic benefit to the patient when implanted.

The invention may also be embodied in a method for implanting biological material in a patient, wherein the biological material disposed in the space defined by the device comprises, for example, autologous, heterologous, syngeneic, allogeneic, or xenogeneic cells/tissue. The cells may be derived from cadaver tissue or from living tissue. The cells may be of non-mammalian or mammalian origin, non-human origin or human origin, self or non-self. The cells may be pluripotent, multipotent, totipotent, or differentiated embryonic or adult stem cells; primary differentiated cells; or immortalized cells, among other cell types. Stem cells may comprise, e.g., cells derived from cord blood, amniotic fluid, menstrual blood, placenta, Wharton's jelly, cytotropoblasts, and the like. The biological material may also comprise any combination of the above-listed cell types. Biological materials of the invention comprise or consist essentially of the above-listed cell types, or may consist of the above-listed cell types.

BRIEF DESCRIPTION OF THE DRAWINGS

These and other objects and advantages of this invention will be more completely understood and appreciated by viewing the following more detailed description of the presently preferred exemplary embodiments of the invention, taken in conjunction with the accompanying drawings, in which:

FIG. 16 shows the representative histopathology of an explanted device from rats receiving syngeneic islets into prevascularized hybrid devices.

FIG. 20 is a table summarizing the survival time of allogeneic islet grafts.

DETAILED DESCRIPTION OF THE INVENTION

Figure 1:
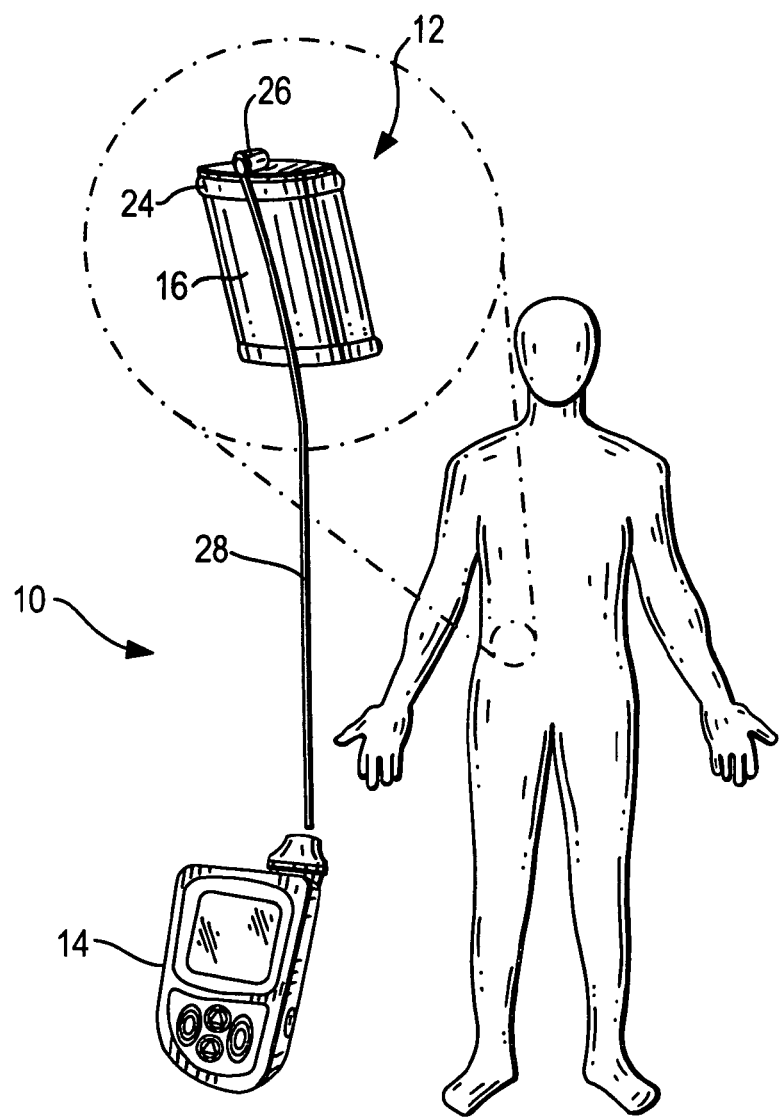
FIG. 1 is a perspective view of a flask-shaped device and pump assembly embodying the invention.

The device may be embodied in, for example, the following designs:

"Flask-Shaped" Device: An embodiment of a flask-shaped hybrid device 10 embodying the invention is illustrated by way of example in FIGS. 1 and 2. The hybrid device comprises an implantable device 12 containing a therapeutic biological material, e.g., cells/tissue or products thereof, either at the time of implantation or in a second stage (after prevascularization of the device), and an external or externally accessible pump or other reservoir 14 for delivery of, e.g., selected nutrients, growth factors and immunomodulatory/immunosuppressive substances to improve vascularization, survival, function and growth of the implanted biological material, e.g. tissues/cells. The implantable device 12 includes a mechanoprotective surface, for example, a porous outer peripheral wall, 16, defining an adjacent, e.g., inner, space or cavity 18. The mechanoprotective surface is perforated sufficiently so as to permit capillaries to grow through the perforations to provide a vascular bed for promoting engraftment of transplanted cells, as described hereinbelow. Thus, the perforations may be, e.g., 100-1000 microns, 300-800 microns, or more preferably 400-700 microns. By way of example, a stainless steel mesh with holes of about 500 microns (diameter) may be provided, but the holes could be slightly smaller or bigger. Any other size that permits adequate vascularization for the specific device location and therapeutic regime is envisioned as being part of the present invention.

In one embodiment, during the vascularization phase, a plunger 20 is disposed within the cavity defined by the mechanoprotective surface 16 to define a vascularization space or gap with the wall of about 1-2 mm. In this regard, it is preferred that the size of the device be limited, preferably to less than 1 cm altogether in thickness, more preferably, less than 0.7 cm, whereas there is 1 to 2 mm of capillary ingrowth all around the plunger, inside the mesh.

Figure 2:
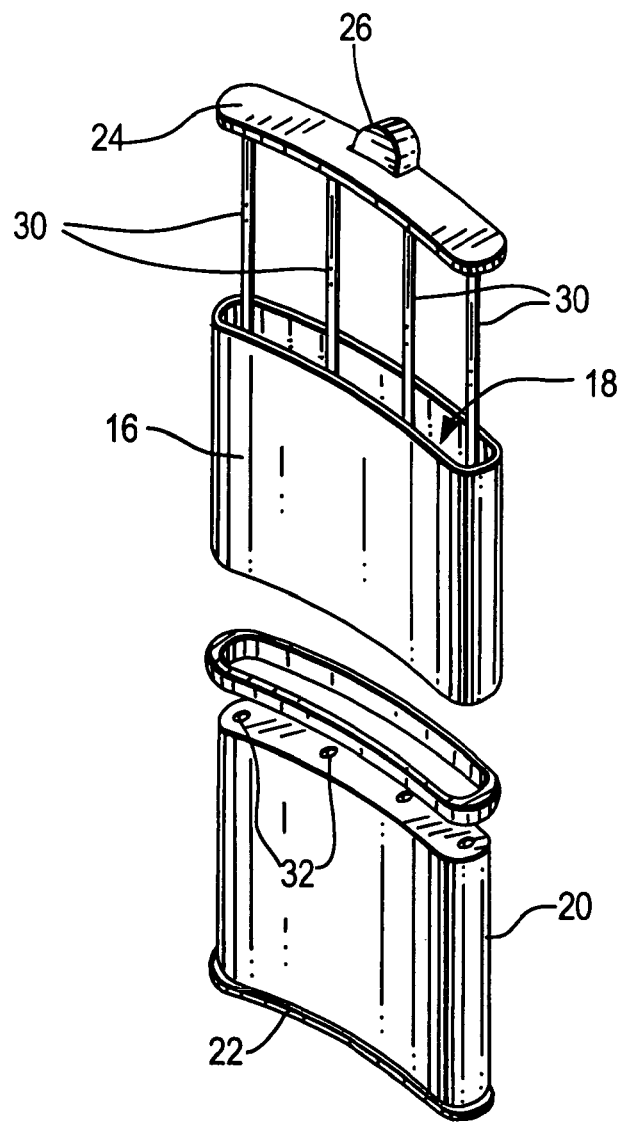
FIG. 2 is an exploded perspective of an embodiment of the flask-shaped device of FIG. 1.

Referring to the illustrated embodiment, one end of the cavity 18 is closed during the vascularization stage with the head or cap 22 of the insert plunger 20 that is selectively disposed within the cavity 18 to define the gap for the new capillaries. A manifold assembly or structure 24 is provided at the opposite end of the device. The manifold structure 24 includes a port 26 for operatively coupling the manifold to a conduit 28 operatively coupled to the pump or reservoir 14, as schematically illustrated in FIGS. 1 and 2, and a manifold cap which serves to distribute the delivered media to a plurality of distribution conduits 30 and to close the respective end of the cavity. In the illustrated embodiment, four conduits 30 are provided for distributing media from the manifold cap into the cavity 18 of the device 12.

Each of the conduits is advantageously micro-perforated for substantially uniform delivery and distribution of the media within the cavity. The micro-perforations may be uniformly distributed. In the alternative, the micro-perforations may be scaled and distributed along the conduit length in a manner to compensate for a decrease in pressure along the length of the conduit in a direction away from the manifold, to ensure uniform distribution of the injected media as described in greater detail below.

It should be noted that in addition to delivery of nutrients, factors, cytokines, drugs, and the like through the manifold structure 24, the mechanoprotective surface and/or the plunger (if provided) may be coated with a suitable media, such as a biocompatible polymer impregnated with suitable drug(s) and/or factor(s) to also act as a regulated or unregulated drug delivery system, particularly when the device is first implanted.

In the embodiment illustrated in FIG. 2, the insert plunger 20 includes longitudinal receptacles 32 disposed for selectively slidably receiving the conduits 30 of the manifold during the vascularization stage. Thus, the plunger 20 can simply be removed in its entirety following the vascularization stage leaving in place the "sprinkler system" defined by the conduits 30 of the manifold 24. A suitable end closure, e.g., a plug corresponding to the external (lower) portion of the plunger, is applied to the device to close that end of the cavity following deposition of the cellular media within the cavity defined by the vascularized bed. This plug (not illustrated) can have little recesses for the extremities of the conduits 30 of the "sprinkler system" to lodge.

Figure 3:
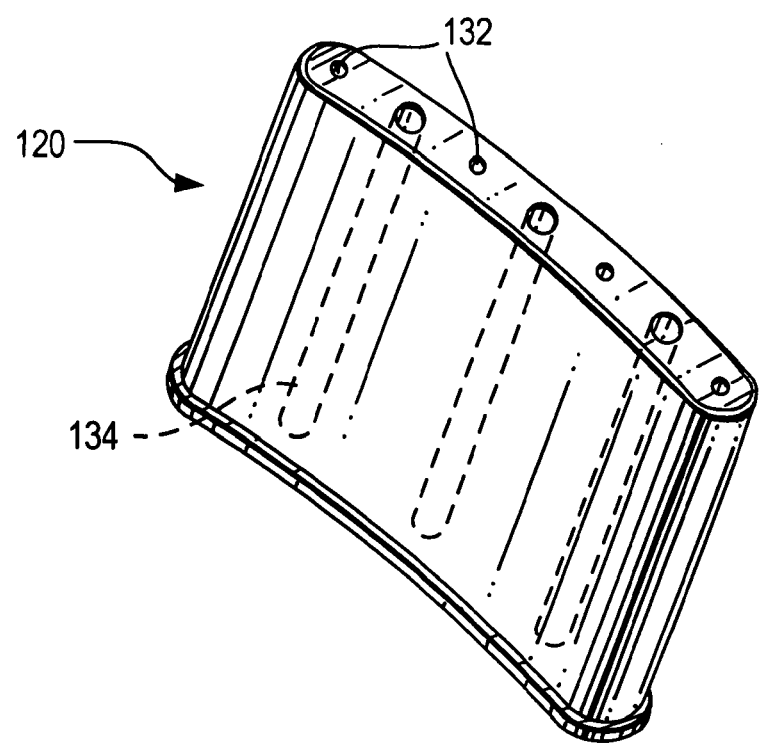
FIG. 3 is a perspective view of a plunger component for the flask-shaped device according to an alternative embodiment of the invention.

In the alternative, a manifold assembly is not separately provided and, instead, once the vascularized bed has been formed, the plunger can be replaced with a manifold structure including a manifold cap and conduits of the type illustrated in FIG. 2. In such a case, the end of the cavity opposite the plunger insertion end may be provided as a fixed, preferably perforated, end wall of the device. Moreover, to provide for delivery during the vascularization stage, in accordance with this embodiment, the plunger preferably itself includes a fluid or slow/sustained release manifold assembly, an example of such a plunger being described below with reference to FIG. 3.

Referring again to the embodiment illustrated in FIG. 2, during the vascularization stage, media can be delivered as deemed necessary or desirable through the manifold 24, making use of the pump 14, to distribute the selected media to the respective conduits 30. Because of the presence of the plunger 20 and the respective receptacles 32 for the conduits, the delivered media will reverse travel out of the receptacles and be distributed on the outer surface of the plunger 20, within the cavity and, depending upon the stage of capillary formation, may pass through the mesh to the surrounding tissues.

Once the vascularization has sufficiently progressed, the plunger plug is surgically accessed and then slidably displaced from within the cavity. The biological material for transplantation, e.g. cells/tissue and/or products thereof, is then disposed within the cavity 18 previously occupied by the plunger 20.

A suitable media may be delivered to travel between the plunger and the new capillaries to facilitate removal of the plunger. In this regard, with reference to the alternate plunger embodiment of FIG. 3, the assembly could include a delivery system with conduits 134 built into the plunger 120, so that they can be used to deliver media to facilitate removal of the plunger 120. Such conduit(s) 134 may also be used to deliver the biological material, e.g. cells/tissue and/or products thereof, at the time of slow withdrawal of the plunger 120. In this case, the biological material, e.g. cells/tissue and/or products thereof, can be progressively loaded while the plunger is slowly withdrawn.

Conduits 134 can be provided so as to alternate with the receptacles 132 for the conduits 30 of the "sprinkler system", e.g. three conduits in the plunger 134 interposed with the four conduits 30 of the "sprinkler system", as illustrated. The three conduits 134 of the plunger would thus allow for solution/cell loading while the plunger 120 is removed. In the alternative, e.g., where the plunger does not incorporate conduit(s) for cellular deposit, as in the embodiment of FIG. 2, the biological material, e.g. cells/tissue and/or products thereof, may be delivered to the device once the plunger is removed by using a small catheter connected to a syringe.

In accordance with another embodiment of the invention, the device is implanted already loaded with biological material, e.g. cells/tissue and/or products thereof, and without any plunger structure. Thus, in this embodiment, the first, pre-vascularization phase is omitted, but the manifold assembly 24 and conduits 30, the so-called "sprinkler system", are still used to feed the implanted biological material with nutrients and growth factors, while favoring vascularization through the delivery of factors such as angiogenic factors.

Where a plunger 20 or 120 is provided, and removed following vascularization, the open end of the device is thereafter suitably closed with, e.g., a Teflon® or GoreTex® closure cap or like closure device, as mentioned above, and the surgical opening is likewise suitably closed. Thereafter, anti-inflammatory, immunosuppressive, or other agents/molecules may be delivered using the pump and distributed via the manifold 24 and distribution conduits 30 to the transplanted biological material. As will be appreciated, the generally flat thin configuration of the device contributes to the delivery of the nutrients from the new capillaries to the deposited biological material.

In certain embodiments, the flask-shaped device contains biological material that is encapsulated.

"Cage-Like" Device: An embodiment of a cage-like hybrid device embodying the invention is illustrated by way of example in FIGS. 4-6. The hybrid device, which may be cylindrical or non-cylindrical, comprises an implantable device 12 containing a therapeutic biological material, e.g. cells/tissue and/or products thereof, either at the time of implantation or in a second stage (after pre-vascularization of the device), and an external or externally accessible pump or other reservoir similar to the one described for the flask-shaped device, for delivery of, e.g., selected nutrients, growth factors and immunomodulatory/immunosuppressive substances to improve vascularization, survival, function and growth of the implanted biological material. The implantable device 12 includes a mechanoprotective surface, for example, a porous, mesh-like outer peripheral wall, 16, defining an adjacent, e.g. inner, space or cavity 18. The mechanoprotective surface is perforated sufficiently so as to allow capillaries to grow through the perforations to provide a vascular bed for promoting engraftment of transplanted cells, as described hereinbelow. Thus, the perforations may be, e.g., 100-1000 microns, 300-800 microns, or more preferably 400-700 microns. By way of example, a stainless steel mesh with holes around 500 microns may be provided, but the holes could be slightly smaller or bigger. Any other size that permits adequate vascularization for the specific device location and therapeutic regime is envisioned as being part of the present invention.

Figure 5A:
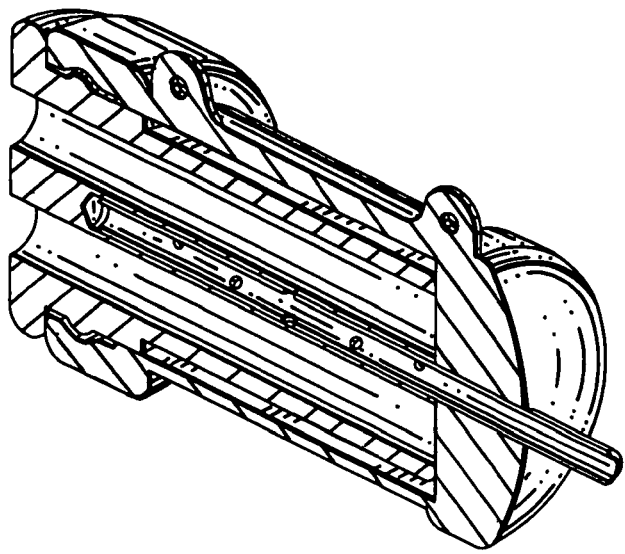
FIG. 5 is a perspective view of an embodiment of the cage-like cylindrical device of FIG. 4.
Figure 5B:
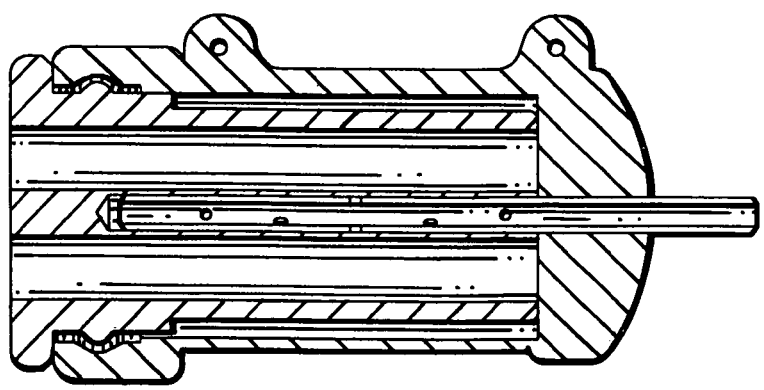

In one embodiment, during the vascularization phase, a plunger 20 is disposed within the cavity defined by the mechanoprotective surface 16 to define a vascularization space or gap with the wall of about 1-2 mm (see FIG. 5). In this regard, it is preferred that the size of the device be limited, preferably to less than 1 cm altogether in thickness, more preferably, less than 0.7 cm, whereas there is 1 to 2 mm of capillary ingrowth all around the plunger, inside the mesh.

Figure 4A:
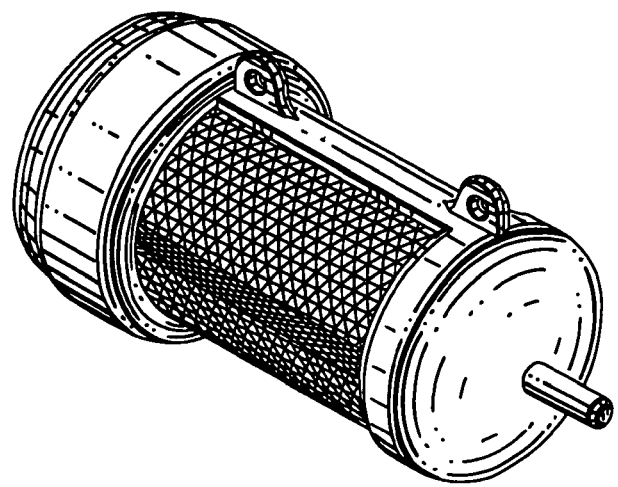
FIG. 4 is a perspective view of a cage-like cylindrical device embodying the invention.
Figure 4B:
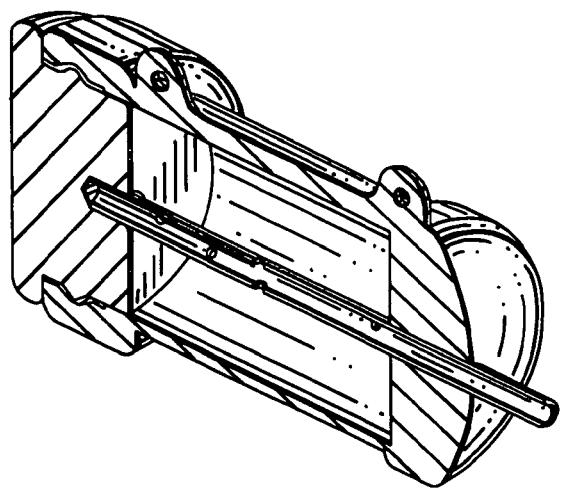

Referring to the embodiments illustrated in FIGS. 4 and 5, one end of the cavity is closed during the vascularization stage, with the head or cap 22 of the insert plunger 20 that is selectively disposed within the cavity connected to a conduit 28 operatively coupled to a pump or reservoir. The delivered media are pumped through this conduit 28 to the distribution conduit 30, which then distributes the media into the cavity of the device. The conduit is advantageously micro-perforated for substantially uniform delivery and distribution of the media within the cavity. The micro-perforations may be uniformly distributed. In the alternative, the micro-perforations may be scaled and distributed along the conduit length in a manner to compensate for a decrease in pressure along the length of the conduit in a direction away from the manifold, to ensure uniform distribution of the injected media as described in greater detail below.

It should be noted that in addition to delivery of nutrients, factors, cytokines, drugs, and the like through the conduit structure, the mechanoprotective surface and/or the plunger (if provided) may be coated with a suitable media, such as a biocompatible polymer impregnated with suitable drug(s)/factor(s) to also act as a drug delivery system, particularly when the device is first implanted.

Figure 6A:
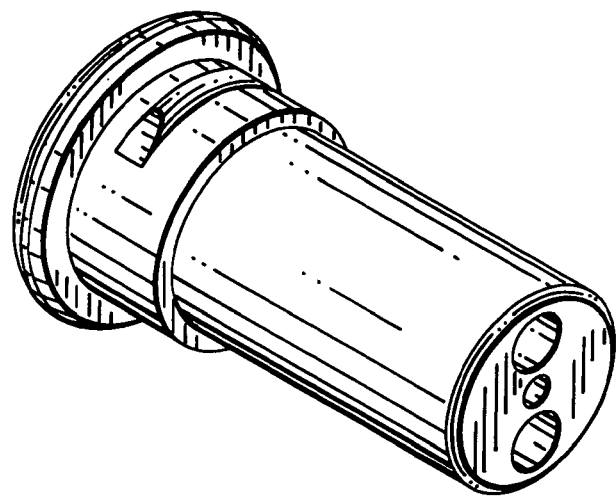
FIG. 6 is a perspective view of a plunger component and a cap/plug component for the cage-like cylindrical device of FIG. 4.
Figure 6B:
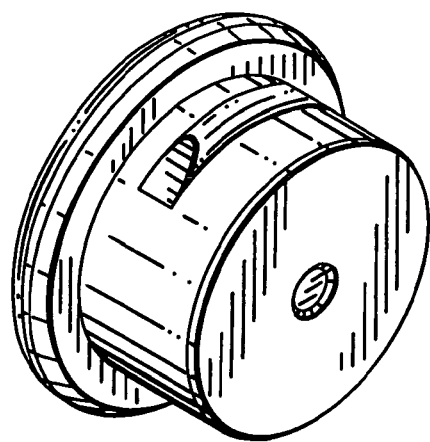

In the embodiment illustrated in FIGS. 5 and 6, the insert plunger 20 includes a longitudinal receptacle 32 disposed for selectively slidably receiving the conduit 30 during the vascularization stage. Thus, the plunger 20 can simply be removed in its entirety following the vascularization stage leaving in place the "sprinkler system" defined by the conduit 30. A suitable end closure 36, e.g., a plug corresponding to the external (lower) portion of the plunger is applied to the device to close that end of the cavity following deposition of the cellular media within the cavity defined by the vascularized bed. This plug can have a little recess 42 for the extremity of the conduit 30 of the "sprinkler system" to lodge.

During the vascularization stage, media can be delivered by the pump or reservoir through the conduit structure as deemed necessary or desirable, to distribute the selected media to the adjacent cavity through the conduit 30. Because of the presence of the plunger 20 and the respective receptacle 32 for the conduit, the delivered media will reverse travel out of the receptacle and be distributed on the outer surface of the plunger 20, within the cavity and, depending upon the stage of capillary formation, may pass through the mesh to the surrounding tissues.

Once the vascularization has sufficiently progressed, the plunger plug is surgically accessed and then displaced (slid out) from within the cavity. The biological material for transplantation, e.g. cells/tissue and/or products thereof, are then disposed within the cavity 18 previously occupied by the plunger 20.

To provide for delivery of media during the vascularization stage, the plunger itself may include an infusion fluid or slow/sustained release assembly, as illustrated in FIGS. 5 and 6. A suitable media may be infused to travel between the plunger and the new capillaries to facilitate removal of the plunger, for example. The assembly could include a delivery system with conduits 34 built into the plunger 20, so that they can be used to deliver media to facilitate removal of the plunger 20. Such conduit(s) 134 may also be used to deliver the biological material, e.g. cells/tissue and/or products thereof, at the time of slow withdrawal of the plunger 20. In this case, the biological material can be progressively loaded while the plunger is slowly withdrawn.

Conduits 134 can be provided so as to alternate with the receptacle 32 for the conduit 30 of the "sprinkler system", e.g. two conduits in the plunger 134 interposed with the one conduit 30 of the "sprinkler system", as illustrated. The two conduits 134 of the plunger would thus allow for solution/cell loading while the plunger 20 is removed. In the alternative, e.g., where the plunger does not incorporate conduit(s) for cellular deposit, the biological material may be delivered to the device once the plunger is removed by using a small catheter connected to a syringe.

Where a plunger 20 is provided, and removed following vascularization, the open end of the device is thereafter suitably closed with, e.g., a Teflon® or GoreTex® closure cap or like closure device 36, as mentioned above, and the surgical opening is likewise suitably closed. Thereafter, anti-inflammatory, immunosuppressive, or other agents/molecules may be delivered using the pump or other reservoir and distributed via the manifold and distribution conduit 30 to the transplanted biological material, e.g. cells/tissue and/or products thereof.

In one embodiment, the cage-like device is neovascularized before deposition of the biological material.

"Coil-Shaped" Device: An embodiment of a coil-shaped hybrid device of the invention is illustrated by way of example in FIG. 7. The hybrid device comprises an implantable device containing a therapeutic biological material, e.g. cells/tissue and/or products thereof, either at the time of implantation or in a second stage (after pre-vascularization of the device), and an external or externally accessible pump or other reservoir (not illustrated) for delivery of, e.g., selected nutrients, growth factors and immunomodulatory/immunosuppressive substances to improve vascularization, survival, function and growth of the implanted tissues/cells. The implantable device includes a mechanoprotective surface, shaped like a coil, for example, defining an adjacent, e.g. inner, space or cavity. The mechanoprotective surface does not completely enclose the adjacent space. Capillaries are thus able to grow, e.g., between the loops of the coil to provide a vascular bed for promoting engraftment of transplanted cells, as described hereinbelow.

In this embodiment, the coil-shaped mechanoprotective surface may be a distribution conduit 30 formed into a coil. A pump or reservoir delivers media through a conduit 28 to the distribution conduit 30, which then distributes the media into and around the cavity of the device. The conduit is advantageously micro-perforated for substantially uniform delivery and distribution of the media within the cavity. The micro-perforations may be uniformly distributed. In the alternative, the micro-perforations may be scaled and distributed along the conduit length in a manner to compensate for a decrease in pressure along the length of the conduit in a direction away from the manifold, to ensure uniform distribution of the injected media as described in greater detail below.

It should be noted that in addition to delivery of nutrients, factors, cytokines, drugs, and the like through the conduit structure, the mechanoprotective surface and/or the plunger (if provided) may be coated with or may additionally contain a suitable media, such as a biocompatible polymer impregnated with suitable drug(s)/factor(s) to also act as a drug delivery system, particularly when the device is first implanted.

During the vascularization stage, media can be delivered by the pump or other reservoir through the conduit structure as deemed necessary or desirable, to distribute the selected media in and around the device through the conduit 30.

Once the vascularization has sufficiently progressed, the plunger plug is surgically accessed and then displaced from within the cavity in a rotational manner. The biological material for transplantation, e.g. cells/tissue and/or products thereof, are then disposed within the cavity previously occupied by the plunger 20 together with other factors, drug and/or nutrient releasing formulations, and other agents as deemed necessary.

Figure 7A:
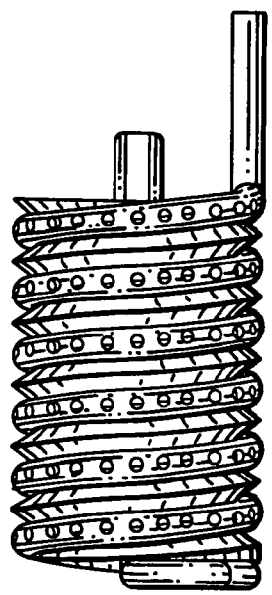
FIG. 7 is an illustration of a coil-shaped device embodying the invention.
Figure 7B:
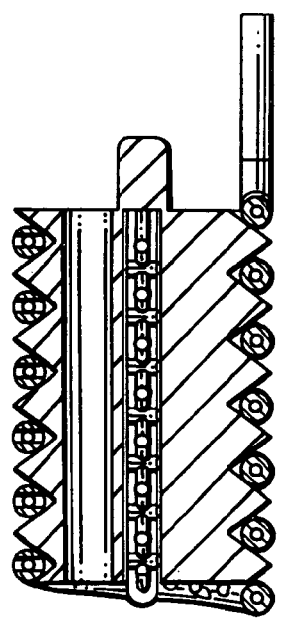

To provide for delivery during the vascularization stage, the plunger itself may include a fluid or slow/sustained release manifold assembly, as illustrated in FIG. 7. A suitable media may be infused to travel between the plunger and the new capillaries to facilitate removal of the plunger, for example. The assembly could include a delivery system with a conduit 134 built into the plunger 20, so that it can be used to deliver media to facilitate removal of the plunger 20. Such conduit(s) 134 may also be used to deliver the biological material, e.g. cells/tissue and/or products thereof, at the time of slow withdrawal of the plunger 20. In this case, the biological material can be progressively loaded while the plunger is slowly withdrawn. In the alternative, e.g., where the plunger does not incorporate conduit(s) for cellular deposit, the biological material can be delivered to the device once the plunger is removed by using a small catheter connected to a syringe.

After biological material has been delivered to the device, anti-inflammatory, immunosuppressive or other agents/molecules may be delivered using the pump or reservoir and distributed via the distribution conduit 30 to the transplanted biological material, e.g. cells/tissue and products thereof.

"Coin-Shaped" Device: An embodiment of a coin-shaped hybrid device embodying the invention is illustrated by way of example in FIGS. 8-11. The hybrid device comprises an implantable device 12 containing a therapeutic biological material, e.g. cells/tissue and/or products thereof, preferably at the time of implantation but potentially in a second stage (after pre-vascularization of the device), and an external or externally accessible pump or other reservoir (not illustrated) for delivery of, e.g., selected nutrients, growth factors and immunomodulatory/immunosuppressive substances to improve vascularization, survival, function and growth of the implanted biological material. The implantable device 12 includes a mechanoprotective surface, for example, a coin-shaped frame, 16, defining and non-completely enclosing an adjacent, e.g. inner, space or cavity 18.

Figure 9:
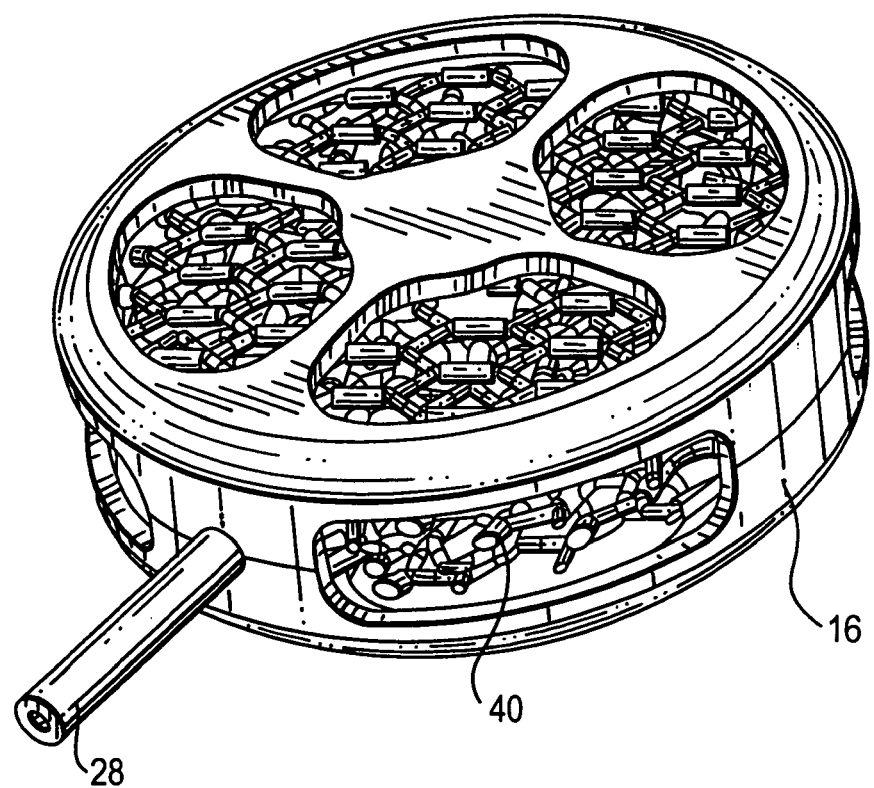
FIG. 9 is a close-up perspective view of the coin-shaped device of FIG. 8.
Figure 10:
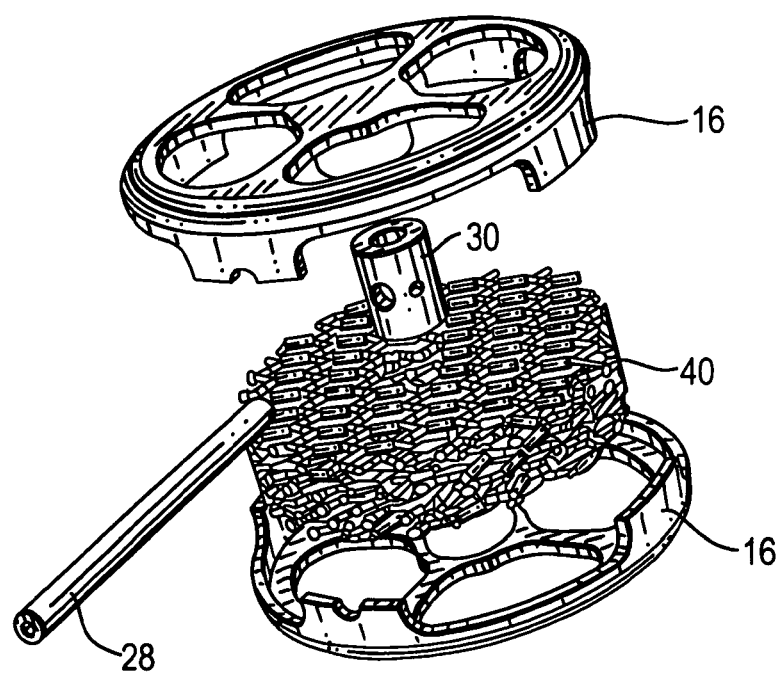
FIG. 10 is an exploded perspective of an embodiment of the coin-shaped device of FIG. 9.

As illustrated in FIGS. 9 and 10, the adjacent, e.g. inner, cavity may comprise a biocompatible matrix material 40 that is implanted with the biological material. The matrix material may comprise, for example, PET or other biocompatible materials, which are preferably biodegradable. Before implantation, the matrix may be seeded with the biological material for implant. Capillaries are able to grow through the matrix material to promote engraftment of the transplanted biological material.

Figure 8:
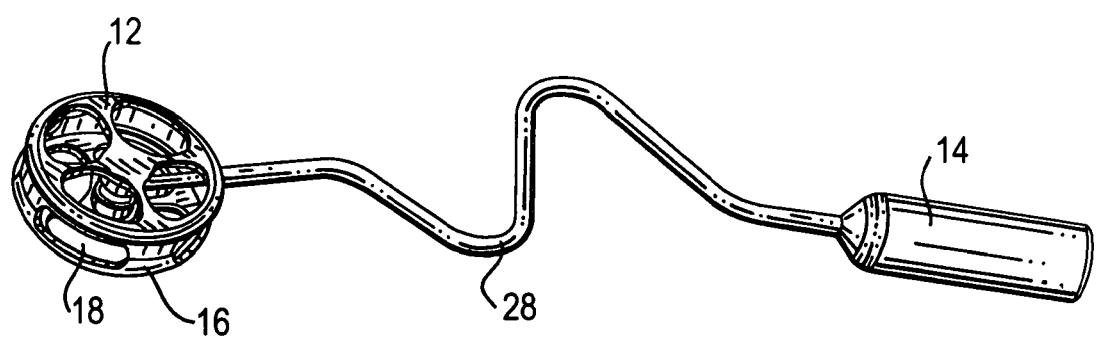
FIG. 8 is a perspective view of a coin-shaped device embodying the invention.

Referring to the embodiment illustrated in FIGS. 8-10, the center "axle" region of the coin-shaped surface 16 forms the distribution conduit 30. A pump or reservoir 14 delivers media through a conduit 28 to the distribution conduit 30, which then distributes the media in and around the cavity 18 of the device. The conduit 30 is advantageously micro-perforated for substantially uniform delivery and distribution of the media within the cavity. The micro-perforations may be uniformly distributed. In the alternative, the micro-perforations may be scaled and distributed along the conduit length in a manner to compensate for a decrease in pressure along the length of the conduit in a direction away from the manifold, to ensure uniform distribution of the injected media.

Figure 11:
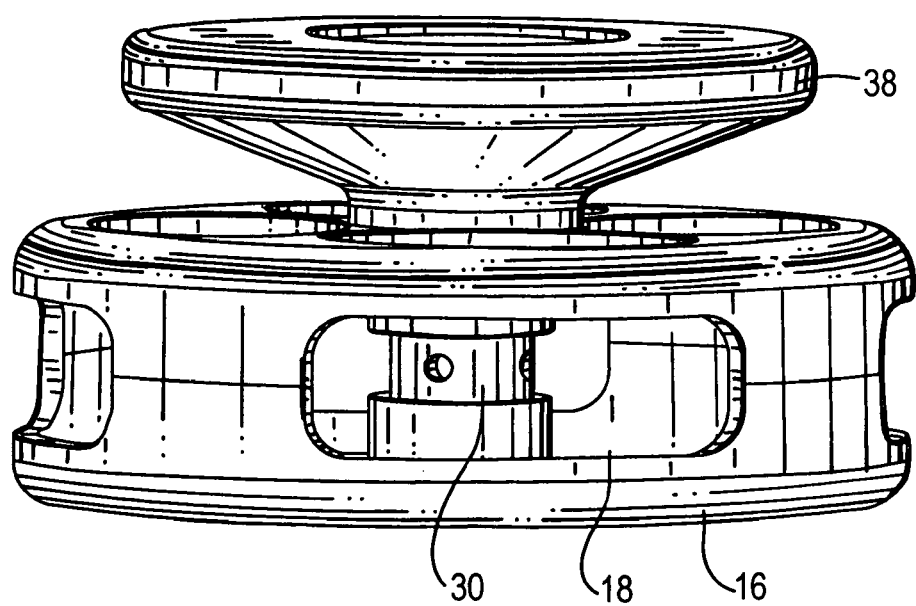
FIG. 11 is an illustration of an alternative embodiment of the coin-shaped device of FIG. 9.

As illustrated in FIG. 11, the coin-shaped device may further comprise a funnel element 38, to facilitate delivery of media to the distribution conduit 30.

After implantation of the device, anti-inflammatory, immunosuppression or other agents/molecules may be delivered using the pump and distributed via the distribution conduit 30 to the transplanted biological material.

Figure 12:
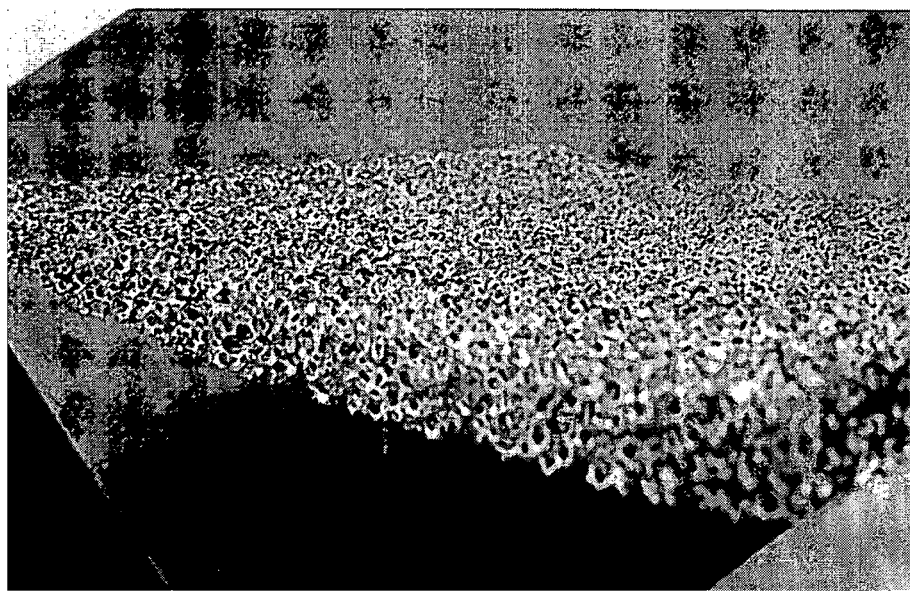
FIG. 12 is a perspective view of a sponge-like device embodying the invention.
Figure 13:
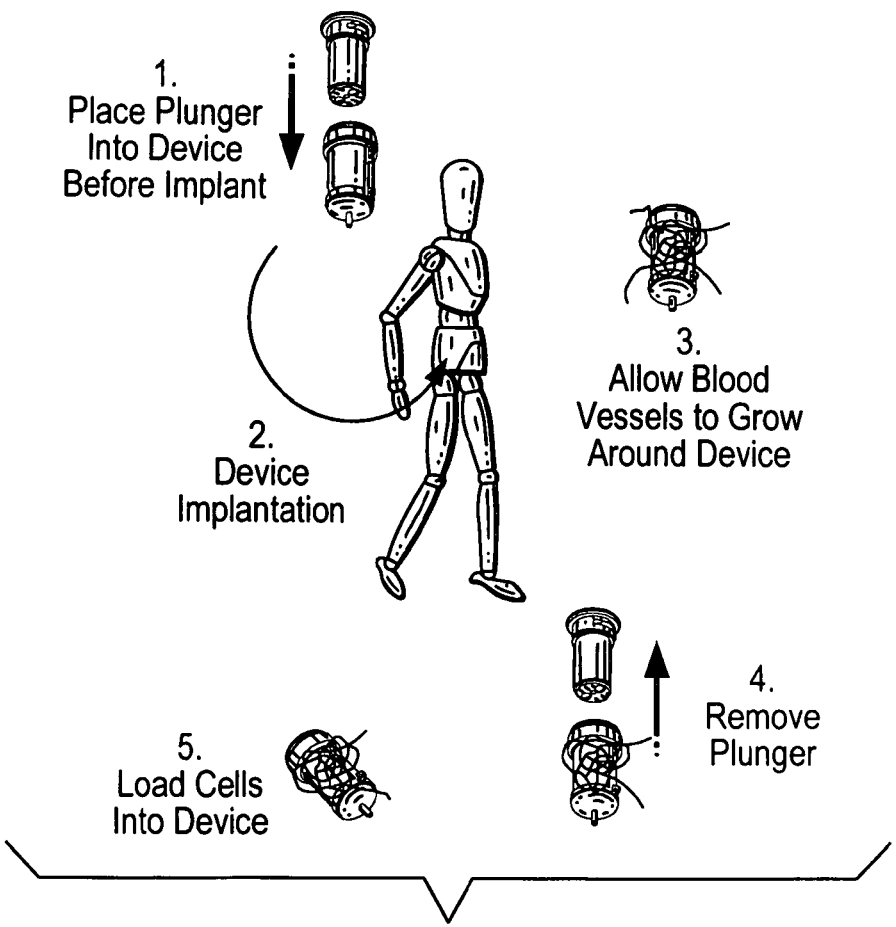
FIG. 13 illustrates the concept of a two-step hybrid device as an alternative site for cellular grafts. The hybrid device is preloaded with a PTFE plunger (1) to prevent the occlusion of its lumen. After implantation (2), the hybrid device is left in place for a sufficient period of time to allow for the recipient tissues to embed it and start vascularization of the walls (3). In a subsequent step, the plunger is removed from the device (4) and islets implanted into the lumen (5) (new FIG. 1)

"Sponge-Like" Device: An embodiment of a sponge-like device of the present invention is illustrated by way of example in FIG. 12. The hybrid device comprises an implantable device 12 containing a therapeutic biological material, e.g. cells/tissue and/or products thereof, at the time of implantation, and an external or externally accessible pump or other reservoir (not illustrated) for delivery of, e.g., selected nutrients, growth factors and immunomodulatory/immunosuppressive substances to improve vascularization, survival, function and growth of the implanted biological material. The implantable device 12 comprises a sponge-like mesh element that may be seeded with the biological material before implantation. Capillaries are able to grow through the mesh material to promote engraftment of the transplanted biological material.

The mechanoprotective surface is perforated sufficiently so as to permit capillaries to grow through the perforations to provide a vascular bed for promoting engraftment of transplanted cells, as described hereinbelow. Thus, the perforations may be, e.g., 100-1000 microns, 300-800 microns, or more preferably 400-700 microns. By way of example, a stainless steel mesh with holes around 500 microns may be provided, but the holes could be slightly smaller or bigger. Any other size that permits adequate vascularization for the specific device location and therapeutic regime is envisioned as being part of the present invention.

In some embodiments, the device may comprise a pump or reservoir that delivers media through a conduit to one or more distribution conduits (similar to those shown in the above-described devices), which then distribute the media in and around the mesh element of the device. The conduit(s) are advantageously micro-perforated for substantially uniform delivery and distribution of the media within the mesh element. The micro-perforations may be uniformly distributed. In the alternative, the micro-perforations may be scaled and distributed along the conduit length in a manner to compensate for a decrease in pressure along the length of the conduit in a direction away from the manifold, to ensure uniform distribution of the injected media.

The mesh element may be non-completely enclosed by, e.g., a disk or other shape with rounded edges, which may be made of plastic materials such as Teflon® and GoreTex®, to eliminate sharp edges in the implant.

After implantation of the device, anti-inflammatory, immunosuppression or other agents/molecules may be delivered using the pump and distributed via the distribution conduit to the transplanted biological material.

In some embodiments, the device of the invention is packaged in a sterile packaging optionally including a label and/or instructions for use of the device. Preferably, the sterile, pre-packaged device is ready for use according to one or more of the methods of the invention. Devices of the invention may but need not necessarily be associated with a biomaterial when the sterilization step is performed. As the skilled artisan will readily appreciate, when one or more biomaterials are associated with the device before it is sterilized, the sterilization method is preferably selected to preserve the activity and/or viability of the biomaterial. Alternatively, devices of the invention may be sterilized before they are associated with a biomaterial according to the invention.

In any of the above embodiments, the device may be implanted already loaded with the biological material, or with the biological material loaded at the time of implantation of the device, without any plunger structure. In such embodiments, the first, pre-vascularization phase, is omitted, but the fluid or slow/sustained release assembly and conduit 30, the so-called "sprinkler system", are still used to feed the implanted cells with, for example, nutrients and growth factors, while favoring vascularization through the delivery of factors such as angiogenic factors.

In any of the above embodiments, biological material may be added to the device, or some or all of the biological material may be replaced within the device, at any time pre- or post-implantation. In one aspect, such addition or replacement could take place, e.g., through the described delivery system.

In any of the above embodiments, the mechanoprotective surface or mesh can be of stainless steel, polymer or any other suitable material that will provide dimensional stability. The surface may be any suitable length and width according to the therapeutic needs in order to adequately favor the production of the therapeutic effect of the selected biological material, for example, a biological factor to be provided by implanted cells. Thus, the device may be, for example, about 3 to 15 centimeters in length and width. This would be a typical range for a device containing cells that deliver a therapeutic product (e.g., islet cells delivering insulin). However, larger devices may be required for implantation of hepatocytes, for example, where the volume of cells to be implanted to provide the desired therapeutic effect, such as to support life, is greater (e.g., in a situation of device implantation for bridging between liver failure and regeneration of the native liver, or between liver failure and allergenic liver transplantation). In these cases, the device could be built to house up to 100-200 ml of cell/tissue volume, therefore requiring larger dimensions. In the case of islets, the total packed cell volume transplanted could be less than, for example, 15 cc of cell/tissue, and typically less than, for example, 7 cc of tissue, 5 cc of tissue or even 1 cc of tissue, depending on the state of the implanted cells and the patient.

The mechanoprotective surface 16 preferably has rounded edges so as to be relatively ergonomic, to be comfortable to the patient while implanted, and to minimize stress concentration. The device, however, may assume any cylindrical or non-cylindrical form, or any matrix or assembly of cylindrical or non-cylindrical forms, provided that the conduit(s) 30 of the fluid or slow/sustained release assembly suitably distribute nutrients, factors, immunosuppressive agents, and other media to the core where the nutrients delivered by the new capillaries will not reach.

As will be appreciated, in embodiments with a porous outer wall or mesh element, the degree of porosity of the outer wall or mesh will determine the size of the neo-formed vessels in the vascular bed. For this reason, the size of the mesh or pores may be determined according to the target application of the encapsulated device structure.

In embodiments that contain closure caps or plugs 36 defined at the respective longitudinal ends of the device, said caps or plugs have a length suitable for the function of sealing to, e.g., the porous wall, and may be, for example, 10% of the length of the device, while having transverse dimensions similar to those of the porous body. If deemed necessary or desirable, additional fastening elements may be provided to suitably secure the plunger, manifold, and/or other end cap in place.

In embodiments that contain a plunger unit 20 or 120, said plunger is preferably a solid component having a shape generally corresponding to that of the mechanoprotective surface 16 but in each direction reduced so as to define a gap with the surface. The plunger may however have a slightly different shape than the outer mechanoprotective surface to facilitate insertion and removal. Thus, for example, the walls of the plunger may be slightly tapered in the insert direction and/or may be grooved or surface treated to facilitate removal. The plunger may be solid or hollow, although solid (except for manifold conduit receptacles and/or its own delivery manifold) is preferred for dimensional accuracy and to minimize the likelihood of media passing into the inside of the plunger and then potentially decomposing over time. The plunger may be made of a material such as plastic, e.g. Teflon® or GoreTex®; a degradable biomaterial that may be angiogenic; or a degradable biocompatible material that may be angiogenic.

In embodiments in which a vascular bed is formed before the biological material is deposited in the device, the thickness of the vascular bed formed by the encapsulation of the device 12 and capillary growth through or around the mechanoprotective surface 16 depends on the gap between the mechanoprotective surface 16 and the plunger 20 or 120, the spacing being determined according to the requirements arising from the end use of the encapsulated device. The transverse dimension of the mechanoprotective surface and the plunger are chosen in accordance with the volume and thickness required, e.g. from about 4 to 15 mm with a separation or gap of about 1 to 2 mm.

In accordance with an embodiment of the invention, the procedure for creating a vascular bed to define a reservoir for receiving biological material and for facilitating long term survival and function of the biological material within the hybrid device comprises implanting the device in the body of the patient with the plunger (when provided) disposed inside or adjacent to the mechanoprotective surface to define a gap for tissue ingrowth. The implant location may be, for example, intraomental (an omental pouch), hepatic, subcutaneous, intraperitoneal, intramuscular, or renal subcapsular, whereby the output of the device may be into the portal system. In preferred embodiments, the implant location is not intravascular.

When implanted in this way, the porous body is overlaid with fibrocollagen by the natural action of the patient's body and a vascular bed develops in the gap between the plunger and the mechanoprotective surface by virtue of the fibrous encapsulation and patient's tissue ingrowth. The tissue ingrowth or vascularization stage may be facilitated or enhanced by delivering suitable factors through the manifold structure using the pump. In addition or in the alternative, the mechanoprotective surface and/or the plunger may be coated with a suitable media, such as a biocompatible polymer impregnated with suitable drug(s)/factor(s) to act as a drug delivery system.

Subsequently, once the fibrocollagen layer has been formed, a partial incision is made in order to expose the plunger access end of the device in order to remove it. If deemed necessary or desirable, suitable media may be delivered through the manifold structure to facilitate plunger removal. When the plunger is removed, a neovascularized receptacle is defined and is suitable for implantation of biological material through the opening in the device. The biological material, which may comprise or consist essentially of biological factor producing cells, and which may in certain embodiments be further encapsulated, and optionally a culture medium selected in accordance with the type of cell to be implanted, is disposed within the receptacle defined by the space left empty by removal of the plunger. The biological factor producing cells act in contact with the neovascularized tissues and the biological factor is absorbed by the patient's bloodstream. Concurrently, immunosuppressive/immuno-regulatory molecules and/or selected nutrients and growth factors that facilitate survival of the transplanted cells and potentially support regeneration/expansion, for example, may be delivered through the manifold structure. As will be appreciated, local delivery of selected nutrients, factors, cytokines, drugs, and the like, will facilitate long term survival and function of transplanted cells while minimizing the side effects of recipient immunosuppression.

The delivery of suitable media via the fluid or slow/sustained release assembly and distribution conduits ensures proper support of the implanted biological material and provides effective localized immunosuppression to reduce or preclude rejection by the host immune system. Because such directed immunosuppression is localized to the implanted biological material, systemic immunosuppression may not be required, or may be required only short term peri-transplant, or may be required at significantly lower doses compared to currently used systemic immunosuppression. The doses locally delivered may be controlled so that, to the extent the immunosuppressive drugs are transported via the new capillaries to elsewhere in the patient's body, the concentration would be such as to reduce and preferably to minimize any adverse affect on the patient. Further, tolerance of the graft may be induced by any method, including but not limited to the delivery of immunosuppressive and/or immunomodulatory factors (including, but not limited to, $T_{reg}$ cells and the factors listed below) into the device for a finite period of time, e.g., during the initial post-transplant period. When such operational tolerance is induced, delivery of immunosuppressive and/or immunomodulatory factors may be reduced, tapered, or stopped entirely In another aspect, cells are tolerized before being deposited into the device. In yet another aspect, cells are tolerized within the device before the device is implanted into the patient.

Encapsulation of the biological material with a biocompatible, immune-protective material may further minimize the need for immunosuppression, either systemically or locally.

Exemplary agents for long term survival and function of transplanted cells include agents for vascularization (e.g., VEGF), anti-inflammatory agents (e.g., anti-TNF-alpha, lysophylline, alpha 1-antitrypsin (AAT), interleukin-10 (IL-10), alpha 1-antitrypsin (AAT), pentoxyfilline, glucocorticoids (e.g., prednisolone, dexamethasone, loteprednol etabonate, flucinolone acetonide, etc.), COX-2 inhibitors, TGF-beta, etc.); cytoprotective/antiapoptotic agents/molecules, tolerance-inducing molecules (e.g., the Power-Mix described in Zheng et al., *Immunity* 19(4):503-514 (2003), or wherein said Power-Mix comprises (1) an agonist to IL-2, immunoglobulin, and/or a fusion protein; (2) antagonist-type IL-15-related cytolytic immunoglobulin and/or a fusion protein; and (3) plus or minus rapamycin); IL-10 and IL-10 fusions; costimulatory blocking agents including antibodies, fusion proteins, small molecules, galectin-1, aptamers, antibodies and aptamers to lymphocyte activation markers (e.g., 4BB1); adhesion molecules (e.g., CD103, etc.) and other molecules involved in the delivery of signals to lymphocytes (e.g., LFA1, LFA3, 4BB1, and CD45, etc.); EBNA-like molecules; IL-35-, IL12-, and IL12-receptor-targeting antibodies and aptamers; anti-IL-17 antibodies; anti-IL-17 receptor antibodies and aptamers; and anti-IL-6 antibodies and IL-6 receptor antibodies and aptamers; etc.); immunosuppressive agents (e.g., oATP, calcineurin inhibitors (e.g., cyclosporine, tacrolimus, etc.), protein kinase C inhibitors (e.g., AEB071, etc.), inhibitors of proliferation signals (e.g., sirolimus, everolimus, JAK3 inhibitors, etc.), inhibitors of nucleotide synthesis (e.g., azathioprine, mycophenolic acid MPA/mycophenolate mofetil MMF, leflunomide, FK778, etc.), glucocorticoids (e.g., prednisolone, dexamethasone, loteprednol etabonate, flucinolone acetonide, etc.), inhibitors of lymphocyte trafficking (such as sphingosine-1-phosphate receptor 1 modulators, etc.); inhibitors of cell surface receptor activation (such as depleting or nondepleting antibodies and fusion proteins including but not limited to Thymoglobulin ATG, muromonab-CD3, alemtuzumab, rituximab, daclizumab, basiliximab, belatacept, campath-1H, Prograf, anti IL-2r, MMF, FTY, LEA, and others, etc.); oxygen generating, releasing (such as encapsulated peroxides, etc.), or transport-enhancing (such as perfluorocarbon PFC) products; and growth factors (e.g., IGF-I, IGF-II, INGAP, exendin-4, GLP-1, HGF, etc.).

In one embodiment, the agent that enhances long term survival and function of transplanted cells is oxidized ATP (oATP). oATP blocks ATP binding and activation of P2X receptors, which are ATP-gated cation channels present on a variety of cell types. P2X receptors are known to be involved in immune/inflammatory processes. Thus, oATP is capable of exerting an anti-inflammatory effect by antagonizing the pro-inflammatory action of ATP on various cells of the immune system implicated in inflammation and tissue destruction.

Administration of oATP systemically or locally (e.g., through a device of the invention) may, alone or in combination with other agents, inhibit T cell-mediated rejection of the transplanted devices of the invention.

The devices and methods of this invention may also be combined with other devices and methods that enhance long term survival and function of transplanted cells. For example, the devices and methods of this invention may be combined with hyperbaric oxygen therapy. In one embodiment, the cells for transplant are treated with a device that provides hyperbaric oxygen to the cells. In another embodiment, the transplant recipient is treated with a device that provides hyperbaric oxygen to the recipient. In another embodiment, the cells for transplant are placed in a device that provides hyperbaric oxygen to the cells, wherein said device is implanted in the transplant recipient. Methods for administering hyperbaric oxygen therapy are known in the art. See, e.g., Juang et al., *Cell Transplantation* 11:95-101 (2002).

The devices and methods of this invention may be used to treat disorders including, but not limited to: diabetes, amyloidosis, immune system disorders, inflammations, chronic pain, arthritis, hypertension, disorders of the nervous system, metabolic disorders, endocrine disorders, lymphoproliferative disorders, myeloproliferative disorders, myelodysplastic syndromes, stem cell disorders, phagocyte disorders, histiocytic disorders, abnormalities of erythrocytes or platelets, plasma cell disorders, acute leukemias, chronic leukemias, malignancies (breast carcinoma, Ewing Sarcoma, neuroblastoma, renal cell carcinoma, etc.), hypothyroidism, hypopituitarism, hypogonadism, graft failure, graft versus host disease (GVD), veno-occlusive disease, side effects from pre-transplant chemotherapy (such as excessive bleeding, infertility, and renal as well as lung and heart complications), and other disorders and diseases that would be recognized by the skilled practitioner.

In certain embodiments in which the biological material comprises cells, the cells may comprise, for example, islet cells, hepatocytes, endocrine cells, immune system cells, thyroid cells, mast cells, endothelial cells, bone marrow cells, dermal cells, nervous system cells and skin cells, among many others that would be recognized by the skilled practitioner. Biological material may comprise or consist essentially of any of these cell types, or may consist of any of these cell types. The implanted cells may be, for example, autologous, heterologous, syngeneic, allogeneic, or xenogeneic. They may be derived from cadaver tissue or from living tissue, from cells of non-human origin or of human origin, from self or non-self. The cells may be pluripotent, multipotent, totipotent, or differentiated embryonic or adult stem cells; primary differentiated cells; or immortalized cells, among other cell types.

To further increase the effectiveness of the treatment, the biological material may comprise or consist essentially of factor-producing cells that have been genetically manipulated by known techniques to produce one or more therapeutic effects on the patient, such as a secreted therapeutic factor. In certain embodiments in which the biological material comprises islets of Langerhans for insulin production, the amount of cells generally desired for the treatment of diabetes referred to hereinabove is about 6,000 to 12,000 islets per kilogram of the patient's weight. In the present invention, these may be combined with one or more helper cells or cell types, e.g., Sertoli cells, in order to immunologically protect the islets from host immune-mediated rejection. In addition, or in the alternative, cells disposed within the device may include cells that produce substances with a different therapeutic activity as in the case of thyroid and parathyroid cells, among others.

Exemplary therapeutic factors which may be delivered by the transplanted cells include, but are not limited to, one or more of: insulin, glucagon, erythropoietin; Factor VIII; Factor IX; hemoglobin; albumin; neurotransmitters such as dopamine, gamma-aminobutyric acid (GABA), glutamic acid, serotonin, norepinephrine, epinephrine, and acetylcholine; growth factors such as nerve growth factor (NGF), brain-derived neurotrophic factor (BDNF), neurotrophin-3 (NT-3), neurotrophin 4/5 (NT-4/5), ciliary neurotrophic factor (CNTF), glial cell line-derived neurotrophic factor (GDNF), cholinergic differentiation factor/leukemia inhibitory factor (CDF/LIF), epidermal growth factor (EGF), insulin-like growth factor (IGF), fibroblast growth factor (FGF), and platelet-derived growth factor (PDGF); pain inhibitors such as Substance P, catecholamines, dynorphins, endorphins, or enkephalins; hormones such as parathyroid hormone or growth hormone; immunomodulators such as granulocyte-macrophage colony stimulating factor (GM-CSF); neuromodulators; lymphokines; cytokines; cofactors; antibodies; aptamers; and enzymes. Choice of one or more therapeutic factors and the concentrations at which they are produced and released from the cells and thereby from the hybrid devices to the patient are dictated by the needs of the patient being treated, and may be readily determined empirically by the skilled practitioner.

In some embodiments, the therapeutic factor has insulin-like or insulin-regulatory activity. In certain embodiments, the therapeutic factor is insulin. In certain embodiments, the therapeutic factor is a precursor form of insulin, such as preproinsulin or proinsulin. In certain embodiments, the therapeutic factor is an insulin chimeric or fusion protein.

In some embodiments, the transplanted cells naturally deliver a therapeutic effect, e.g. by naturally expressing or delivering one or more therapeutic factors. In some embodiments, the implanted cells are genetically modified to deliver a therapeutic benefit; e.g. by transfection into the cells of one or more genes capable of expressing in a regulated or non-regulated manner, one or more therapeutic factors.

In some embodiments, the therapeutic factor(s) are released from the implanted cells due to the receipt of a stimulus or signal from the host (e.g., changes in blood levels of glucose, hormones, metabolic signaling agents, chemical signaling molecules, etc.).

In some embodiments, the therapeutic effect comprises regulation of insulin levels in the blood. In certain embodiments, the therapeutic effect comprises regulation of glucose levels in the blood. In other embodiments, the therapeutic effect comprises regulation of levels of one or more other biological response regulators in the blood of the patient.

In some embodiments, prior to delivery into the hybrid device, the cells/tissue, products thereof, and/or other non-cellular biological materials may be encapsulated by a physical barrier comprising biocompatible materials to improve viability and/or to provide protection from the host environment. As well as providing structural integrity, cell distribution and mechanical strength, such encapsulation can protect the implanted cells from the immune response of the host.

Materials preferred for the encapsulation of living cells are biocompatible, do not interfere with the function of the transplanted cells, and reduce, minimize or eliminate an immune response in the patient. Materials and methods for encapsulating cells are well known in the art. Common materials used for encapsulation include, but are not limited to: natural materials such as alginate (Sun et al., *J Control Release* 2:137-141

(1985); Grant et al., *FEBS Letters* 32(1):195-198 (1973); Martinsen et al., *Biotech Bioeng* 33:79-89 (1989); Lanza et al., *Transplantation* 59(10):1485-1487 (1995)), agarose (see, e.g., Tun et al., *Cell Transplant* 5 (Suppl. 1):S59-63 (1996); Shoichet et al., *Biotechnol Bioeng* 50:374-381 (1996); Iwata et al., *J Biomed Mater Res* 26(7):967-977 (1992)), collagen (see, e.g., Puviani et al., *Int J Artif Organs* 22(11):778-785 (1999); Ratcliffe, *Matrix Biol* 19(4):353-357 (2000); Jain et al., *Transplantation* 59(3):319-324 (1995)), and elastin (see, e.g., Geutjes et al., *Adv Exp Med Biol* 585:279-295 (2006); Berglund et al., *Tissue Eng* 10(9-10):1526-1535 (2004); Lu et al., *Biomaterials* 25(22):5227-5237 (2004)); natural-derived materials such as Biodritin® (see, e.g., U.S. Pat. No. 6,630,154); mimetics such as PureMatrix (see, e.g., Ramachandran et al., *Biodrugs* 20(5):263-269 (2006); Leach et al., *Acta Biomater* 1(2):155-164 (2005); Ma et al., *Tissue Eng* 11(1-2):101-109 (2005); Yamaoka et al., *J Biomed Mater Res A* 78(1):1-11 (2006)); or synthetic polymers such as poly(lactic acid) (see, e.g., Watanabe et al., *Biomacromolecules* 3(5):1109-1114 (2002); Chen et al., *Biomaterials* 25(11):2065-2073 (2004); Fukuhira et al., *Biomaterials* 27(9):1797-1802 (2006)), poly(lactide-co-glycolides)(PLGA) (see, e.g., Li et al., *J Biomed Mater Res A* 80(1):226-233 (2007); Kang et al., *J Biomater Sci Polym Ed* 17(8):925-939 (2006); Ellis et al., *J Biotechnol Bioeng* 96(1):177-187 (2006)), poly(ethylene glycol) (PEG) (see, e.g., Contreras et al., *Surgery* 136:537-547 (2004); Panza et al., *Biomaterials* 21:1155-1164 (2000); Xie et al., *Biomaterials* 26:403-412 (2005); Chen et al., *Biodrugs* 15(12):833-847 (2001)), or combinations thereof (see, e.g., Lee et al., *Biomaterials* 27(30):5268-5276 (2006); Chandy et al., *Artif Organs* 23(1):894-903 (1999); Crooks et al., *J Biomed Mater Res* 24(9):1241-1262 (1990); Lee et al., *J Biomed Mater Res* 62:372-377 (2002)).

In certain embodiments, the matrix material comprises poly(ethylene glycol) (PEG). In certain embodiments, the matrix material consists essentially of poly(ethylene glycol) (PEG). In certain embodiments, the matrix material consists of poly(ethylene glycol) (PEG).

In certain embodiments, the matrix material comprises alginate. In certain embodiments, the matrix material consists essentially of alginate. In certain embodiments, the matrix material consists of alginate.

In some embodiments, the matrix materials used for encapsulation may be chemically altered to contain functional groups for the stabilization of the encapsulation matrix. Further, the materials may be chemically altered to allow attachment of therapeutic factors or other molecules that associate with such therapeutic factors (i.e., receptors or affinity agents) (see, e.g., Kim et al., *Biomacromolecules* 4(5):1214-1223 (2003)). Therapeutic factors may be incorporated into the matrix via covalent cross-linking, emulsification, ionic interactions, specific affinity interations, simple entrapment, and any combination thereof.

In one embodiment, anti-inflammatory molecules are tethered to the surface of the matrix to reduce the host inflammatory response to the implant. Exemplary anti-inflammatory agents include corticosteroids (dexamethasone, cortisol, prednisolone, loteprednol etabonate, flucinolone acetonide, and others), interleukin-1 (IL-1), interleukin-10 (IL-10), alpha 1-antitrypsin (AAT), lisofylline, pentoxyfilline, COX-2 inhibitors, interleukin-1 receptor antagonist peptide (IRAP), interleukin-10 (IL-10), alpha 1-antitrypsin (AAT), TGF-beta; antibodies to IL-1, interferon-gamma, and TNF-alpha; anti-tissue factor, and complement inhibitors. In another embodiment, extracellular matrix (ECM) molecules such as collagen type I or IV, laminin, fibronectin, or arginine-glycine-aspartate peptides are incorporated on the surface of the matrix (Beck et al., *Tissue Eng* 13(3):1-11 (2007)).

In certain embodiments, encapsulated cells may take the form of, for example, a macrostructure scaffold, a microcapsule, a nanocapsule, a linked extruded capsule, or combinations thereof. These forms differ in many variables, including size, volume of cells contained, and strength and diffusion characteristics.

In one embodiment, the biological materials to be implanted are encapsulated in a macrostructure scaffold. Macrostructure scaffolds of the hybrid device preferably provide mechanical integrity to the biological material, prevent clumping and clustering of the biological material, and may also comprise a scaffold for cell migration and/or angiogenesis. The size of macrostructure scaffolds may vary but is limited by the accessibility of oxygen and nutrients to the cells farthest from the surface of the scaffold.

Common methods used to generate macrostructure scaffolds include the injection of matrix materials and/or the biological material for implant into molds, followed by the initiation of matrix formation such that the materials take on the shape of the mold. Matrix formation may be initiated by methods including, but not limited to: temperature change (Yang et al., *Biomaterials* 15(2):113-120; Sefton et al., *J Control Release* 65(1-2):173-186 (2000)), photopolymerization (Andreopoulos et al., *Biomaterials* 27(11):2468-2476 (2006); Kwon et al., *Biomaterials* 27(7):986-995 (2006)), covalent crosslinking (Geutjes et al., *Adv Exp Med Biol* 585:279-295 (2006); Orban et al., *J Biomed Mater Res A* 68(4):756-762 (2004); Hada et al., *Blood* 68(1):95-101 (1986)), or ionic crosslinking (Zmora et al., *Biomaterials* 23(20):4087-4094 (2002); Li et al., *Biomaterials* 26(18):3919-3928 (2005)). Depending on the application, the matrix material of the scaffold may be degraded by the surrounding tissue in vivo or may retain long-term stability.

In another embodiment, the biological material is encapsulated in microcapsules. Microcapsules are typically smaller in size than macrostructure scaffolds, ranging from approximately 3 millimeters (mm) to less than 500 micrometers in diameter. This limits the barrier distance between the encapsulated cells and the surrounding environment. The microcapsule "shell" surrounding the implanted cells is semi-permeable, where the cells can exchange oxygen, nutrients, and other small molecules with the host environment, but attack of the encapsulated cells by large host immune system components such as immune cells and antibodies is prevented.

The microcapsule may further comprise bioactive molecules that increase cell viability. For example, the microcapsule may contain an oxygen binding agent such as perfluorocarbon (PFC), to increase the oxygen level throughout the microcapsule and improve viability of the encapsulated cells.

Common methods used to produce microcapsules include but are not limited to: parallel air flow (Sun et al., *Methods Enzymol* 137:575-580 (1988); Esch et al., *Biopolymers* 50(3):227-237 (1999)), electrostatic droplet formation (Lewinska et al., *Artif Cells Blood Substit Immobil Biotechnol* 32(1):41-53 (2004); Sun et al., *Tissue Eng* 9 (Suppl 1):S65-75 (2003)), emulsification (Tun et al., *Cell Transplant* 5 (Suppl. 1):S59-63 (1996); Iwata et al., *Diabetes* 38 (Suppl. 1):224-225 (1989)), and centrifugation (Crooks et al., *J Biomed Mater Res* 24(9):1241-1262 (1990)). Linked capsules can be generated using common extrusion methods or adaptations on the parallel air flow and electrostatic droplet formation references provided above. Microcapsule matrices may be further stabilized by cross-linking via photoinitiation (Cruise et al., *Biotechnol Bioeng* 57:655-665 (1998); Lu et al., *Biotechnol*

Bioeng 70(5):479-483 (2000)) or other methods (Dusseault et al., Biomaterials 26(13):1515-1522 (2005)).

In an exemplary embodiment, the biological material is encapsulated in nanocapsules. Nanocapsules are typically smaller in size than microcapsules and may encpasulate a single cell or a cluster of cells. The semi-permeable nanocapsule shell can be as thin as 1 nanometer (nm), effectively minimizing the barrier distance and allowing for optimal exchange of small molecules between the encapsulated cells and the host environment while still limiting attack by larger immune cells and antibodies.

Nanocapsules can be produced by depositing thin layers of a biocompatible material around a single cell or a cluster of cells. These biocompatible materials include but are not limited to: poly(ethylene glycol) (PEG), alginate, and Biodritin®, a more biocompatible alginate derivative. In one embodiment, the biocompatible material comprises PEG, alginate, and/or Biodritin®. In another embodiment, the biocompatible material consists essentially of PEG, alginate, and/or Biodritin®. In another embodiment, the biocompatible material consists of PEG, alginate, and/or Biodritin®.

Common techniques employed for depositing nanoscale layers on cell surfaces include: covalent conjugation (Contreras et al., Surgery 136:537-547 (2004); Panza et al., Biomaterials 21:1155-1164 (2000); Xie et al., Biomaterials 26:403-412 (2005)), electrostatic interaction (Krol et al., Nano Lett 6(9):1933-1939 (2006); Miura et al., Biomaterials 27(34): 5828-5835 (2006)), free-radical cross-linking (Cruise et al., Cell Transplant 8(3):293-306 (1999); Hill et al., Ann NY Acad Sci 831:332-343 (1997)), and emulsion (Crooks et al., J Biomed Mater Res 24(9):1241-1262 (1990); Sefton et al., J Control Release 65(1-2):173-186 (2000)).

In certain embodiments, the biological material is "nano-coated" by extrusion with alginate via a 20-gauge needle into a 1.1% $CaCl_2$ solution, wherein the droplet size is controlled by parallel airflow.

In certain embodiments, the biological material is nano-coated by water soluble molecules that are selected from the group consisting of: poly(ethylene glycol) (PEG); poly(vinyl alcohol) (PVA); poly(vinylpyrrolidone) (PVP); poly(thyloxazoline) (PEOX); poly(amino acids); polysaccharides such as alginate, hyaluronic acid, chondroitin sulfate, dextran, dextran sulfate, heparin, heparin sulfate, heparan sulfate, chitosan, gellan gum, xanthan gum, guar gum, water soluble cellulose derivatives and carrageenan; and proteins such as gelatin, collagen and albumin.

In a preferred embodiment of the nanocapsules useful in accordance with the present invention, the water soluble molecules comprise poly(ethylene glycol) (PEG). In another preferred embodiment, the water soluble molecules consist of or consist essentially of poly(ethylene glycol) (PEG).

In another preferred embodiment of the nanocapsules useful in accordance with the present invention, the water soluble molecules comprise alginate. In another preferred embodiment, the water soluble molecules consist of or consist essentially of alginate.

In some embodiments, "active" nanocapsules can be made by attaching bioactive molecules to the nanocapsule surface. For example, anti-inflammatory molecules can be tethered to the surface of the matrix to reduce the host inflammatory response to the encapsulated biological material, such as encapsulated cells/tissue and/or products thereof, reducing damage to the encapsulated biological material. Exemplary anti-inflammatory agents include corticosteroids (dexamethasone, cortisol, prednisolone, loteprednol etabonate, flucinolone acetonide, and others), interleukin-1 (IL-1); interleukin-10 (IL-10); alpha 1-antitrypsin (AAT); lysophylline; pentoxyfilline; COX-2 inhibitors; interleukin-1 receptor antagonist peptide (IRAP); interleukin-10 (IL-10); alpha 1-antitrypsin (AAT); TGF-beta; antibodies to IL-1, interferon-gamma, and TNF-alpha; anti-tissue factor; and complement inhibitors. In another embodiment, extracellular matrix (ECM) molecules such as collagen type I or IV, laminin, fibronectin, or arginine-glycine-aspartate peptides are incorporated on the surface of the matrix (See, e.g., Beck et al., Tissue Eng 13(3):1-11 (2007)).

EXAMPLE 1

Regulation of Glucose Levels in Animals Implanted with a Hybrid Device Comprising Islets of Langerhans Lewis rats were rendered diabetic with intravenous injections of streptozotocin and used as islet graft recipients only if nonfasting glycemic values were ≥350 mg/dL on whole blood samples. Half of the animals were then implanted 40 days before islet transplantation with a hybrid device of the invention in the subcutaneous space of the infrascapular area. The pre-implantation facilitated embedding of the device perforated walls into the collagen-rich and well-vascularized tissues of the recipient. During this time, the adjacent space of the device contained a Teflon® plunger to prevent recipient tissue from obstructing the space.

Syngeneic islets were then isolated by methods known in the art. A partial incision was made in each of the animal subjects, and the Teflon® plunger was removed from animal subjects implanted with the device. Using a small catheter and a syringe, the islets (3,000 IEQ) were deposited into the neovascularized space left by the plunger in animals implanted with the device, while in animals not implanted with the device, the islets were implanted directly in the subcutaneous space of the infrascapular area.

Figure 14:
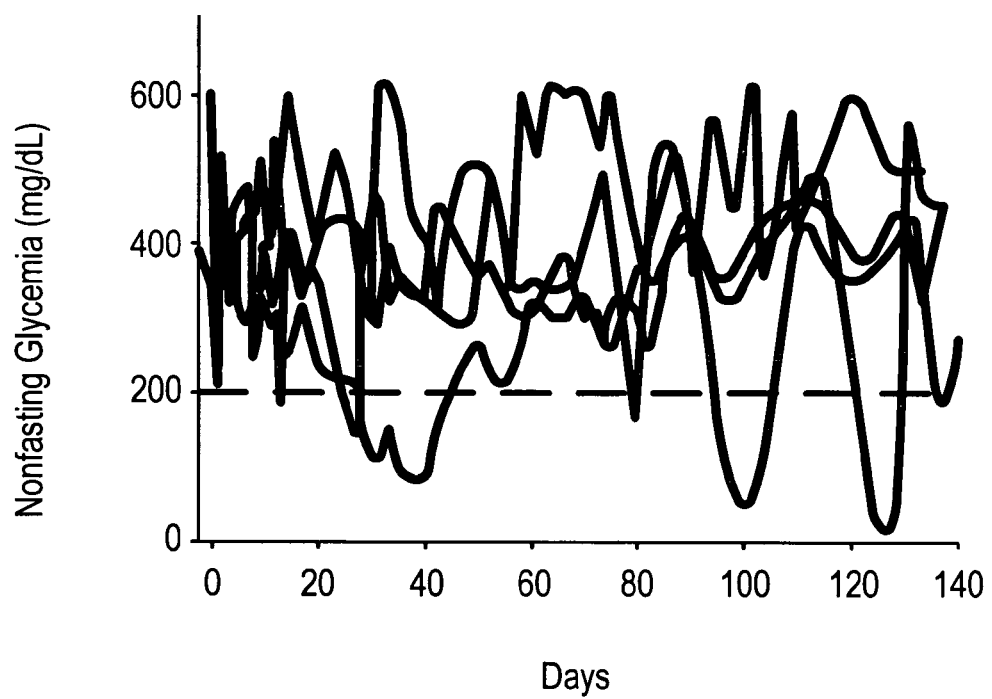
FIG. 14 is a graph showing the non-fasting glycemia (mg/dL) in chemically-induced diabetic rats over time after transplantation of syngeneic islets.
Figure 15:
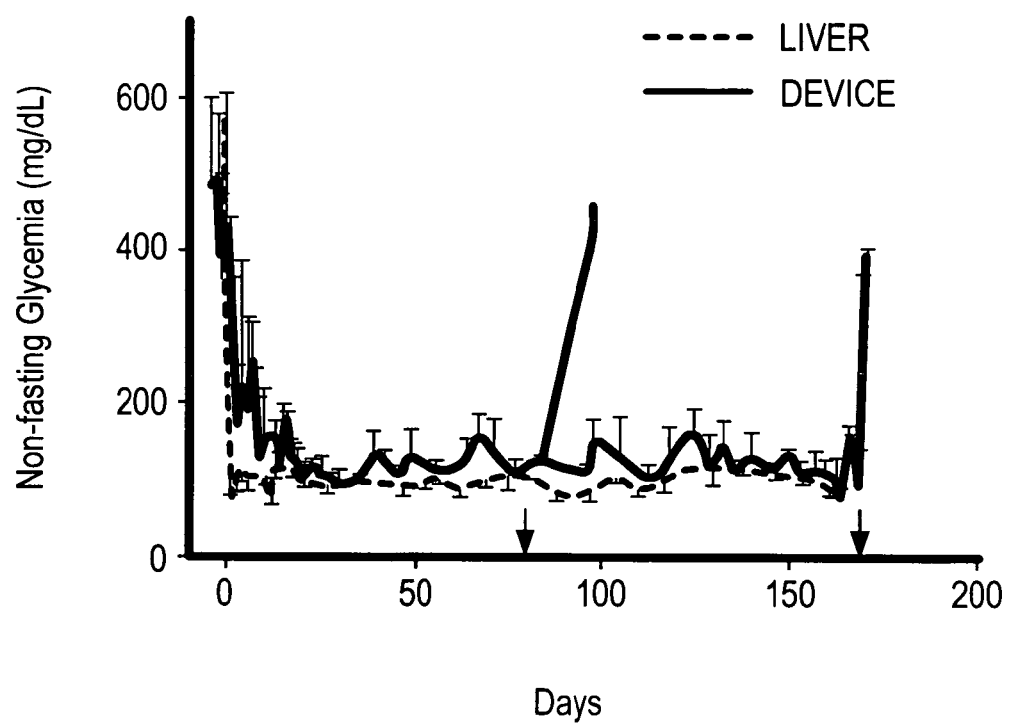
FIG. 15 is a graph showing the non-fasting glycemia (mg/dl) in chemically-induced diabetic rats over time after transplantation of syngeneic islets in a hybrid device of the invention.

After transplantation, the animals' glucose levels were monitored daily. In animals that were implanted with islets alone (without the device), only 30% achieved normoglycemia after transplantation (see FIG. 14). In contrast, in animals implanted with the device, 100% showed sustained (long-term) normoglycemia (nonfasting glycemic values<200 mg/dL) after transplantation (see FIG. 15, solid red line). Removal of the graft-bearing devices (arrows) resulted in prompt return to hyperglycemia, therefore confirming that the normalization of glycemic values was due to the function of islets implanted into the prevascularized device. Recipients of syngeneic islets (3,000 IEQ) in the liver also showed reversal of diabetes and sustained (long-term) normoglycemia (FIG. 15, dotted blue line). Devices were explanted>80 days from islet transplantation, and tissue explanted from the devices was stained with trichrome and for insulin and von Willebrand factor immunoreactivity. Well preserved islets were observed (FIGS. 16a and b) with intense insulin immunoreactivity (FIG. 16b) as well as a rich vascular network (FIGS. 16a and c).

EXAMPLE 2

Figure 17A:
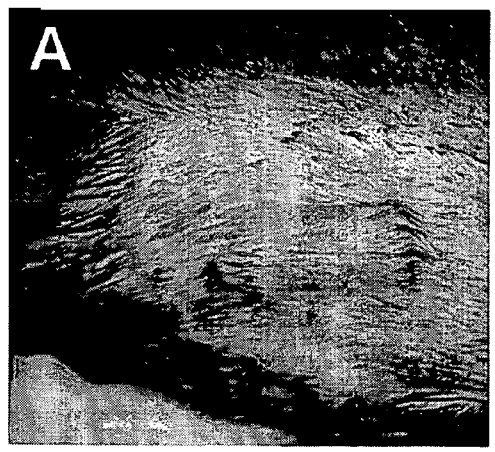
FIG. 17 shows a representative hybrid device implanted in the subcutaneous space of a C57BL/6 mouse. Appearance of the device from the skin>80 days from implantation (A). Incision of the skin allowed exposure of the subcutaneous space and of the device showing intense vascular networks around the connective tissue embedding the device (B).
Figure 17B:
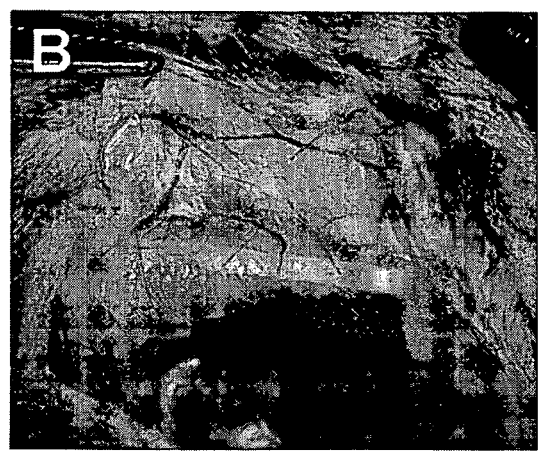
Figure 18:
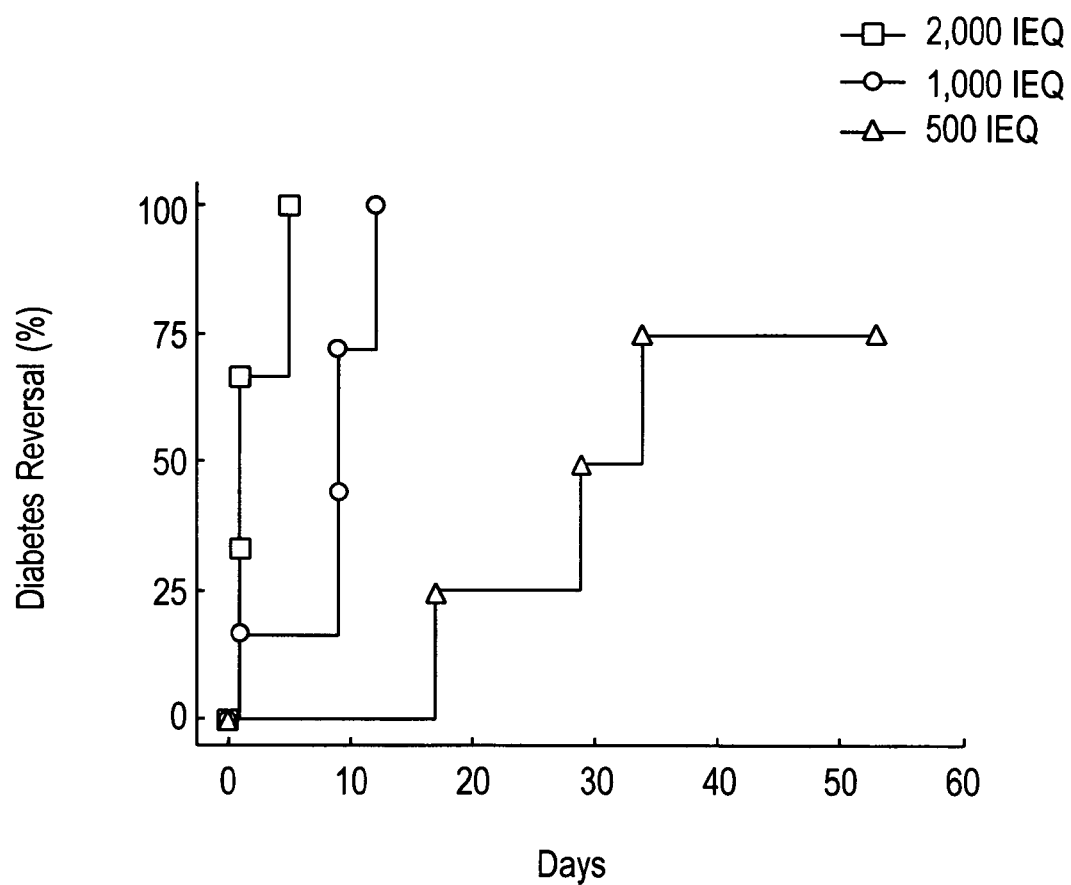
FIG. 18 shows reversal of diabetes in C57BL/6 mice receiving syngeneic islet grafts into prevascularized hybrid devices.

Dose-Dependent Reversal of Diabetes in Animals Implanted with a Hybrid Device Comprising Islets of Langerhans C57BL/6 mice were rendered diabetic with intravenous injections of streptozotocin and implanted with a hybrid device of the invention in the subcutaneous space. Incision of the skin>80 days from implantation allowed exposure of the subcutaneous space and of the device, showing intense vascular networks around the connective tissue embedding the device (FIG. 17). Titration experiments with increasing numbers of syngeneic islets (500, 1,000, and 2,000 IEQ) were performed by depositing the islets into the prevascularized hybrid devices six weeks after implantation. As seen in FIG. 18, the time to diabetes reversal was dependent upon the deposited dose of islets.

EXAMPLE 3

Transplant Viability in Animals Implanted with a Hybrid Device Comprising Islets of Langerhans, with or without Systemic Immunosuppression Lewis rats were rendered diabetic with intravenous injections of streptozotocin. Six weeks before islet transplantation, the chemically-diabetic animals were implanted with a hybrid device of the invention in the subcutaneous space of the infrascapular area. The pre-implantation facilitated embedding of the device perforated walls into the collagen-rich and well-vascularized tissues of the recipient. During this time, the adjacent space of the device contained a Teflon® plunger to prevent recipient tissue from obstructing the space.

Figure 19:
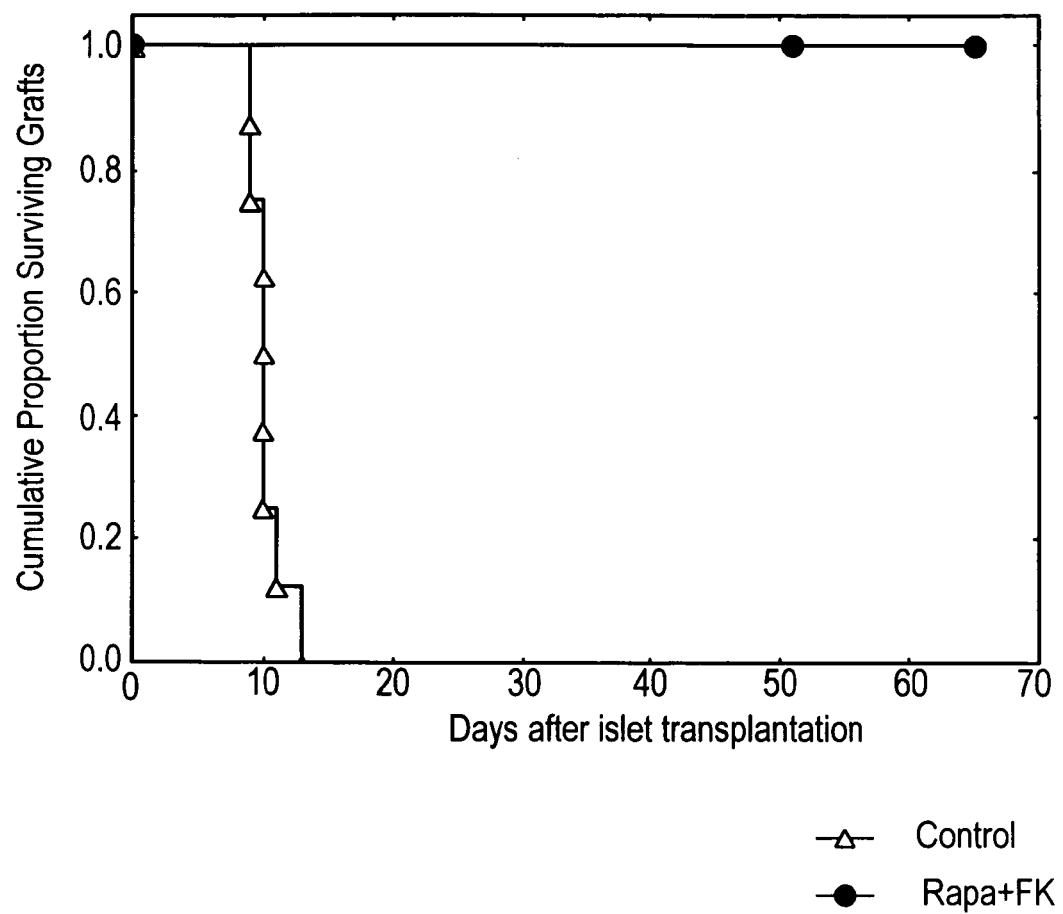
FIG. 19 shows allogeneic rat islet allograft survival in hybrid devices under systemic immunosuppression. Long-term graft function (>80 days) was observed after allogeneic islet transplantation into immunosuppressed recipients (solid circles), while untreated controls rejected the transplant within 12 days (open triangles).

Allogeneic islets (approximately 7,000 IEQ) from Wistar Furth donor rats were then deposited into the neovascularized spaces of the hybrid devices, using the methods described in Example 1. Post-transplantation, half of the animal subjects were treated systemically with immunosuppressive agents starting on the day of islet transplantation (day 0) and consisting of sirolimus (rapamycin; administered by oral gavage at 3.0 mg/kg on days 0, 1, 2, and every other day thereafter) and tacrolimus (FK506; FK; 1.0 mg/kg SC daily), while the other half remained untreated. Untreated subjects invariably rejected islet allografts within 12 days of transplant (FIG. 19, open triangles), while animals treated systemically with sirolimus and tacrolimus invariably showed sustained graft function for >80 days (FIG. 19, solid circles; FIG. 20).

Figure 21:
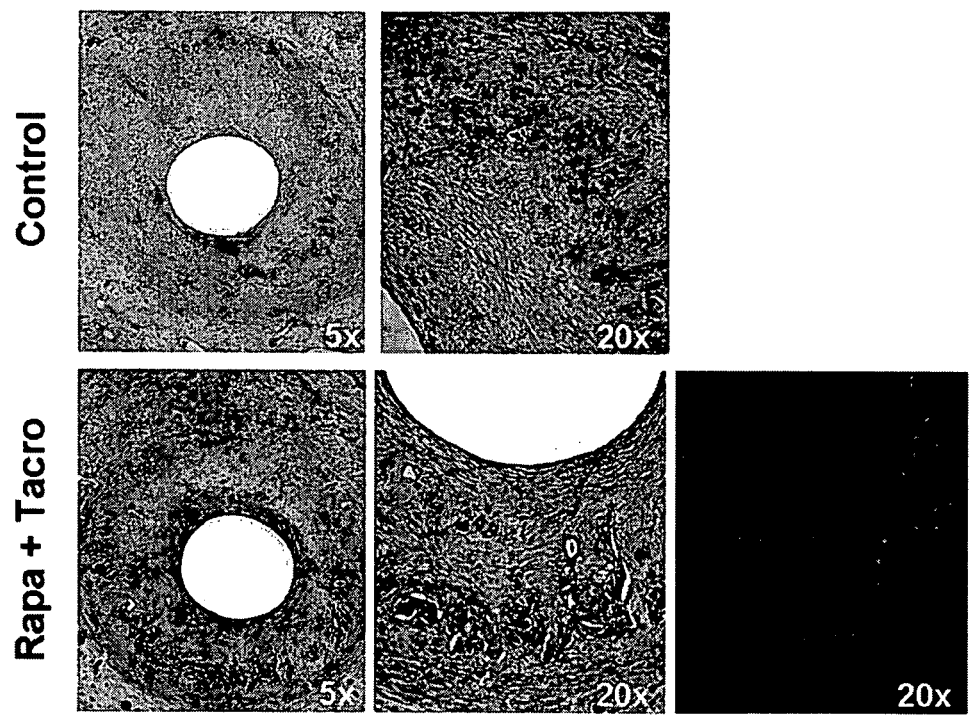
FIG. 21 shows representative histopathological assessment of allogeneic islet grafts implanted into hybrid devices under systemic immunosuppression in rats. Histopathology of the grafted tissue in hybrid devices received 18 days after transplantation showed loss of islets and fibrosis after rejection in control, untreated animals (upper panels). Explants from animals receiving chronic systemic immunosuppression displayed well-preserved islet structures in the hybrid devices with minimal or absent mononuclear cell infiltrate (lower panels) and intense insulin immunoreactivity (lower right panel: red=insulin; blue=nuclear staining).

Devices were explanted at the time of rejection (approximately day 12) from control animals and >80 days from immunosuppressed animals. Histopathology of the grafted tissue in explanted hybrid devices showed loss of islets and fibrosis after rejection in control, untreated animals (FIG. 21, upper panels). Explants from animals receiving chronic systemic immunosuppression displayed well-preserved islet structures in the hybrid devices with minimal or absent mononuclear cell infiltrate (lower panels) and intense insulin immunoreactivity (FIG. 21, lower right panel: red=insulin; blue=nuclear staining).

Figure 22:
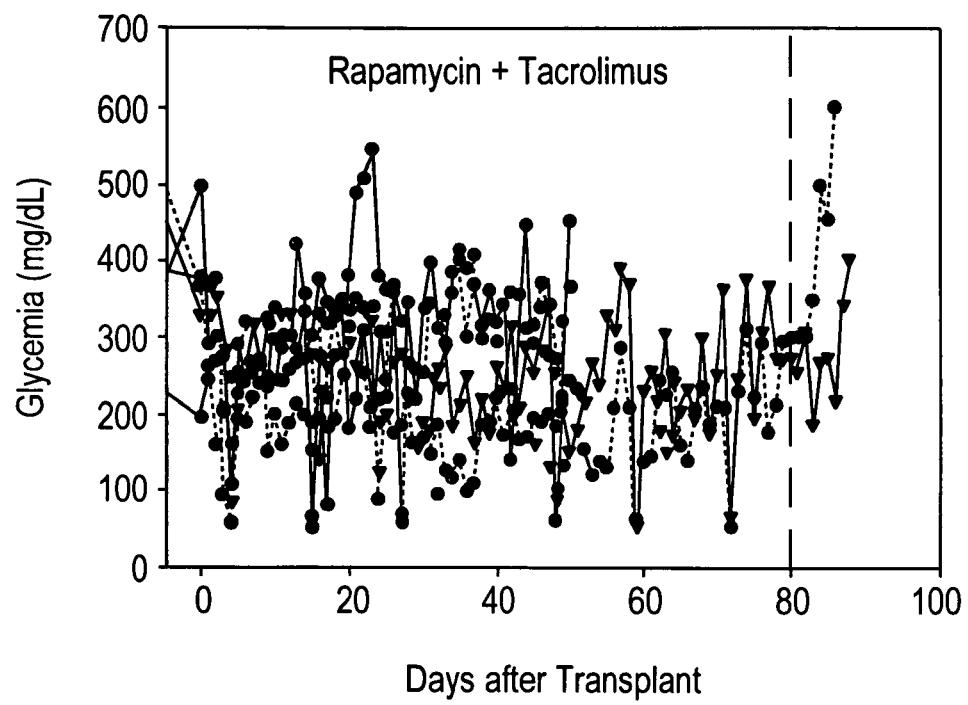
FIG. 22 shows glycemic profiles of Lewis rat recipients of allogeneic islets in hybrid devices under systemic immunosuppression. Long-term graft function (>80 days) was invariably observed after allogeneic islet transplantation into immunosuppressed recipients. None of the animals achieved stable nonfasting euglycemia during the follow-up despite transplantation of 7,000 IEQ, while displaying euglycemia at fasting. Removal of the hybrid device or withdrawal of immunosuppression after 80 days consistently resulted in increased glycemic values.
Figure 23A:
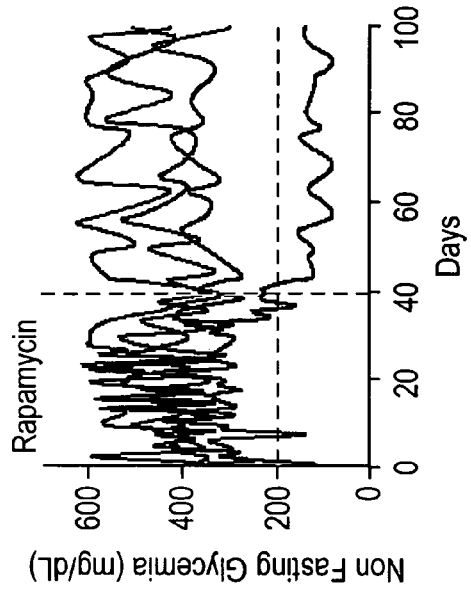
FIG. 23 shows the effects of conventional immunosuppressive drugs given at the time of syngeneic islet transplantation on the engraftment and graft function in rats. Control animals achieved and maintained normoglycemia long-term, whereas animals receiving rapamycin, tacrolimus, or both showed only partial or primary non-function while under treatment. Withdrawal of immunosuppression did not improve graft function, with only ¼ animals in the groups receiving either of the single-drug treatment achieving normoglycemia at later times.
Figure 23B:
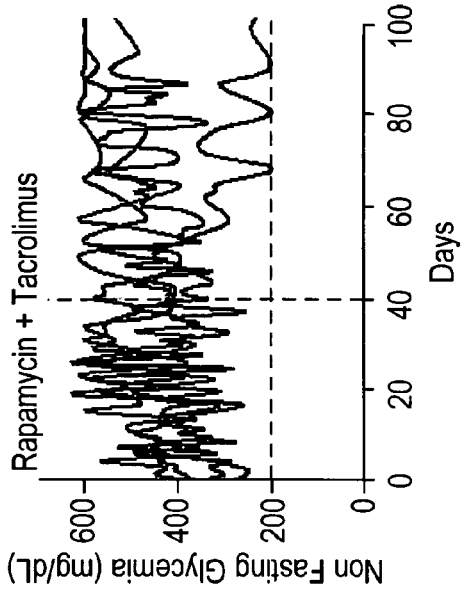
Figure 23C:
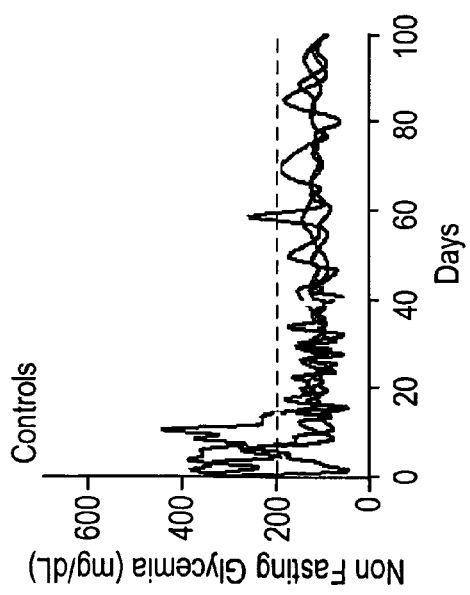
Figure 23D:
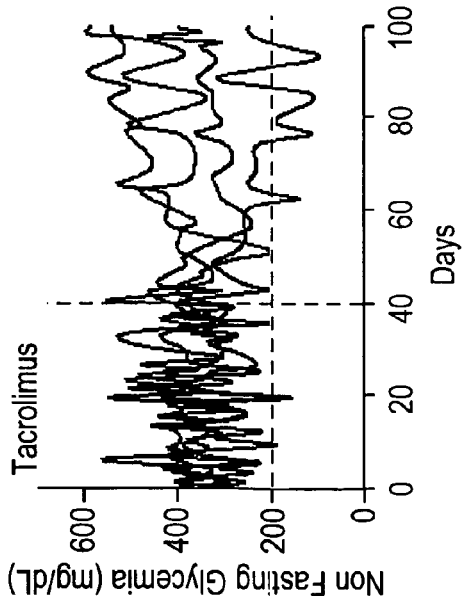

Long-term graft function (>80 days) was invariably observed after allogeneic islet transplantation into immunosuppressed recipients. Notably, none of the animals achieved stable nonfasting euglycemia during the follow-up despite transplantation of 7,000 IEQ, while displaying euglycemia at fasting (FIG. 22). Removal of the hybrid device or withdrawal of immunosuppression after 80 days consistently resulted in increased glycemic values. These data indicate that prolonged survival of islet allografts implanted into hybrid devices can be obtained under systemic immunosuppression, and also highlight the potential negative impact of selected systemic immunosuppression on islet engraftment and function.

EXAMPLE 4

Effects of Conventional Systemic Immunosuppression on Islet Engraftment and Function in Animals Implanted with a Hybrid Device Comprising Islets of Langerhans To assess the impact of conventional systemic immunosuppression on islet engraftment and function in prevascularized hybrid devices, we carried out syngeneic islet transplantation in chemically-diabetic Lewis rats that were treated with either rapamycin or tacrolimus (alone or in combination) as described in Example 3, starting from the day of islet transplantation, for 40 days. Control animals received no treatment. As shown in FIG. 23, following islet transplantation (3,000 IEQ), control animals achieved and maintained long-term normoglycemia, whereas animals receiving either or both immunosuppressive drugs showed only partial function or primary non-function while under treatment. Withdrawal of immunosuppression did not improve graft function, with only ¼ animals in the groups receiving either of the single-drug treatments achieving normoglycemia at later times. These data suggest that the conventional systemic immunosuppression used may adversely affect engraftment of islets into a hybrid device, and that this may lead to substantial (and possibly irreversible) loss of functional islet mass.

Figure 24A:
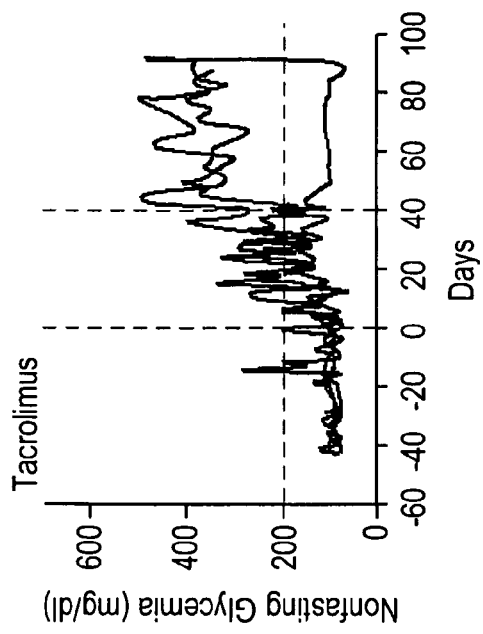
FIG. 24 shows the effects of selected immunosuppressive drugs on the function of already engrafted syngeneic islets in rats. Systemic immunosuppression administered for 40 days resulted in impaired graft function in all groups receiving tacrolimus alone or in combination with rapamycin, while in the rapamycin alone group, only ⅓ of the animals displayed dysfunction while under treatment. After drug withdrawal, the animals receiving the rapamycin alone and ⅓ in the group receiving tacrolimus alone returned to normoglycemia, while none of the animals in the combination group recovered function.
Figure 24C:
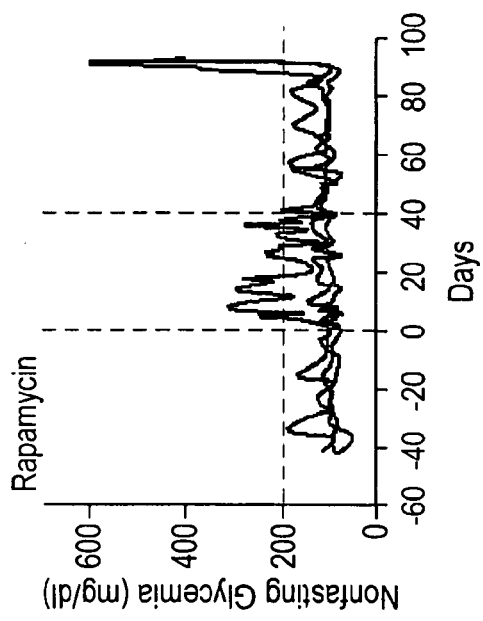
Figure 24B:
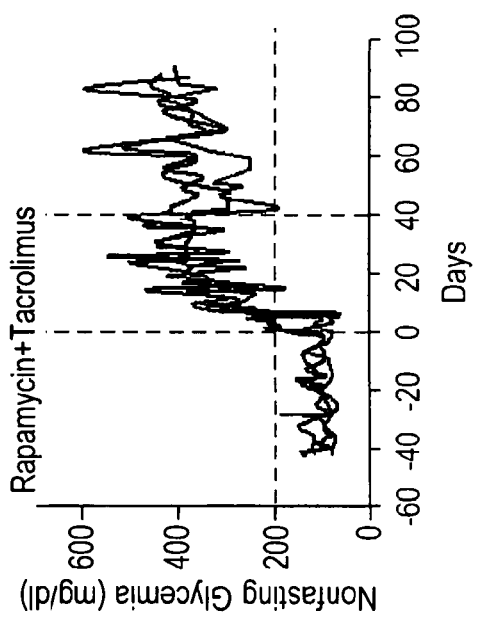

We also explored the effects of rapamycin and tacrolimus on syngeneic islet graft function in animals possessing an already-engrafted functional syngeneic islet graft, ≥40 days post implantation of the graft. As shown in FIG. 24, systemic immunosuppression administered for 40 days resulted in impaired graft function in all groups receiving tacrolimus alone or in combination with rapamycin, while in the rapamycin alone group only ⅓ of the animals displayed dysfunction while under treatment. After drug withdrawal, the animals receiving rapamycin alone and ⅓ of the animals receiving tacrolimus alone returned to normoglycemia, while none of the animals in the combination group recovered function. Our data corroborate previous studies on the toxicity of tacrolimus and suggest that combination with rapamycin may exacerbate such effects.

EXAMPLE 5

Figure 25:
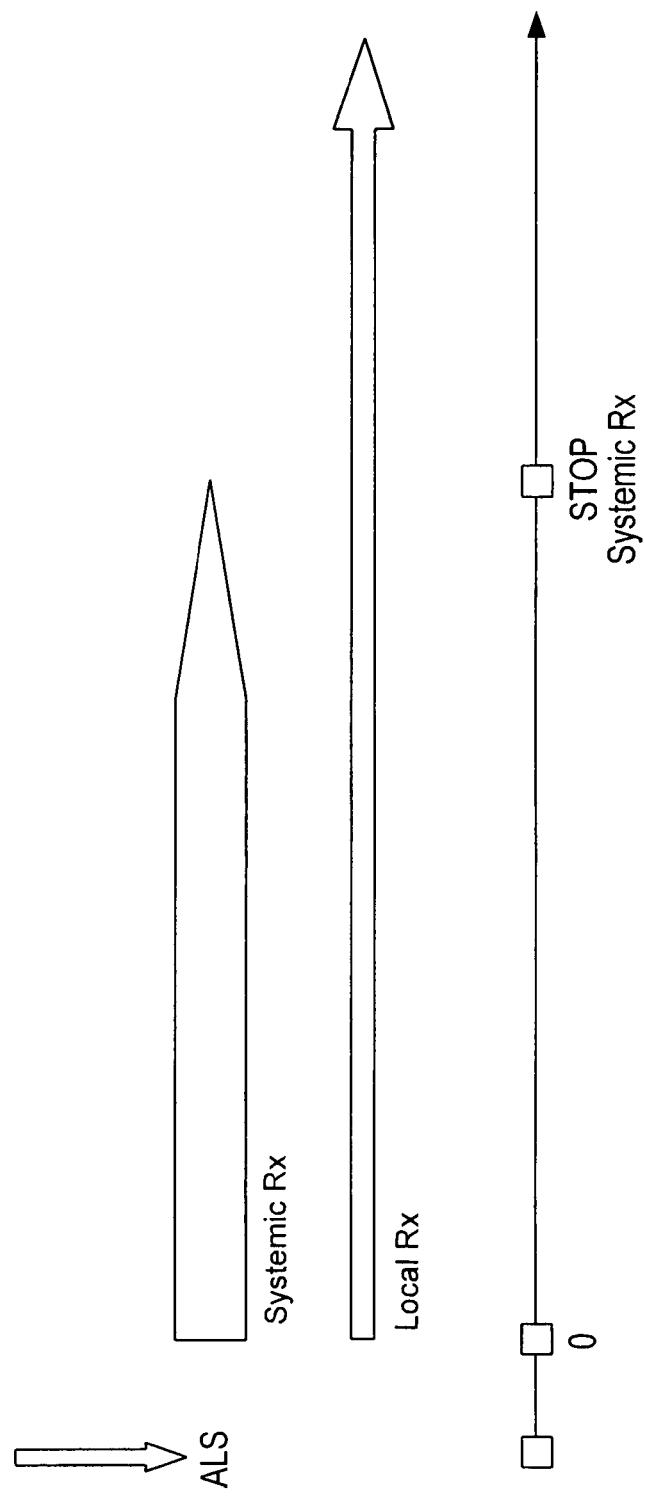
FIG. 25 shows an experimental protocol for transient systemic immunosuppression combined with extended localized immunotherapy in rodents.

Transplant Viability of Animals Implanted with a Hybrid Device Comprising Islets of Langerhans, with Local Immunosuppression Lewis rats were chemically induced to be diabetic by intravenous injection of streptozotocin. Forty days before islet transplantation, the rats were implanted with a hybrid device of the invention with a plunger-containing device in the subcutaneous space as described in Example 3. Allogeneic islets (7,000 IE isolated from Wistar Furth rats) were then deposited into the neovascularized spaces of the hybrid devices, and after the transplantation, the animals' glucose levels were monitored daily as described in Examples 1 and 3. Post-transplantation, all animals received systemic immunosuppression treatment consisting of a single-dose induction treatment with T-cell depleting anti-lymphocyte serum (ALS) given intravenously on day −3. Starting on the day of islet transplantation, systemic maintenance immunosuppression with mycophenolic acid (MPA, 20 mg/kg) was given daily orally for at least three weeks. Pilot islet allotransplantation under the kidney capsule of diabetic recipients showed that sustained graft function for >60 days could be achieved under this regimen of chronic systemic immunosuppression, whereas control untreated animals invariably rejected within 10 days from islet implantation. After at least two weeks of treatment, systemic immunosuppression was tapered and discontinued, while the local immunosuppression was maintained. For example, a typical weaning protocol of systemic treatment consisted of 25% reduction of MPA for two consecutive days over an 8-day period. FIG. 25 illustrates an experimental protocol of transient systemic immunosuppression combined with local extended immunotherapy.

Figure 26:
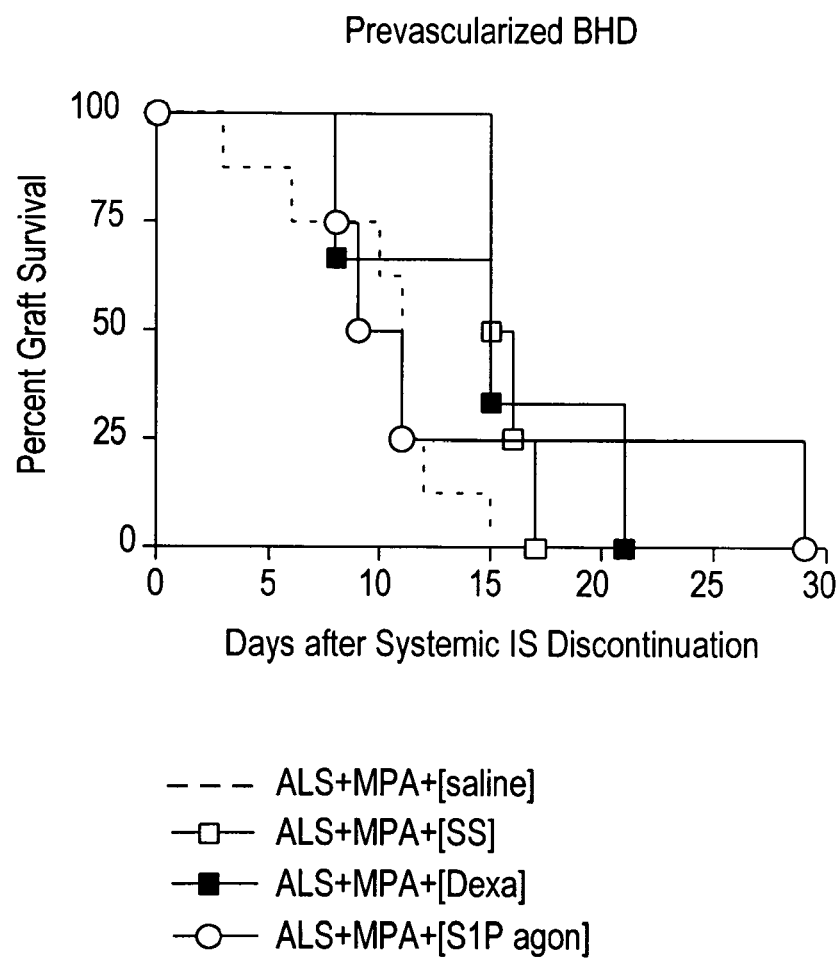
FIG. 26 shows allogeneic islet graft survival under local immunosuppression in rats. The graph summarizes the proportion of survival (actuarial Kaplan-Meier curves) of islet allografts after completion of the weaning protocol of systemic immunosuppression. The data in the brackets indicate local treatment via osmotic pump for each experimental group. The use of local delivery of steroids as either dexamethasone phosphate (Dexa, 20 mg/L) or loteprednol etabonate (soft steroid SS; 0.2, 0.5, and 10 mg/L) as well as of a sphingosine-1-phosphate receptor agonist (S1P agon; 50 mg/L) allowed for a sizable extension of allograft survival in these experiments.

Starting on the day of islet transplantation, animals also received local immunosuppression delivered using a micro-osmotic pump such as the Alzet® 100 microL volume, 2-week continuous infusion, 0.25 microL/h delivery rate model 1002 pump (Durect Corp., Cupertino, Calif.). Both the device and the pump were implanted in the dorsal region of the rodents, and they were connected via a PE tubing. Animals were divided into controls receiving either local saline or no treatment and treatment groups receiving various immunosuppressive agents such as, for example, dexamethasone phosphate (20 mg/L), loteprednol etabonate (0.2, 0.5, and 10 mg/L), or a sphingosine-1-phosphate (S1P) receptor agonist (50 mg/L) from the micro-osmotic pump. In a number of animals, this local treatment allowed for a clear extension of allograft survival compared to the control animals that invariably rejected their graft within 2 weeks from the discontinuation of the systemic immunosuppression (FIG. 26).

Figure 27:
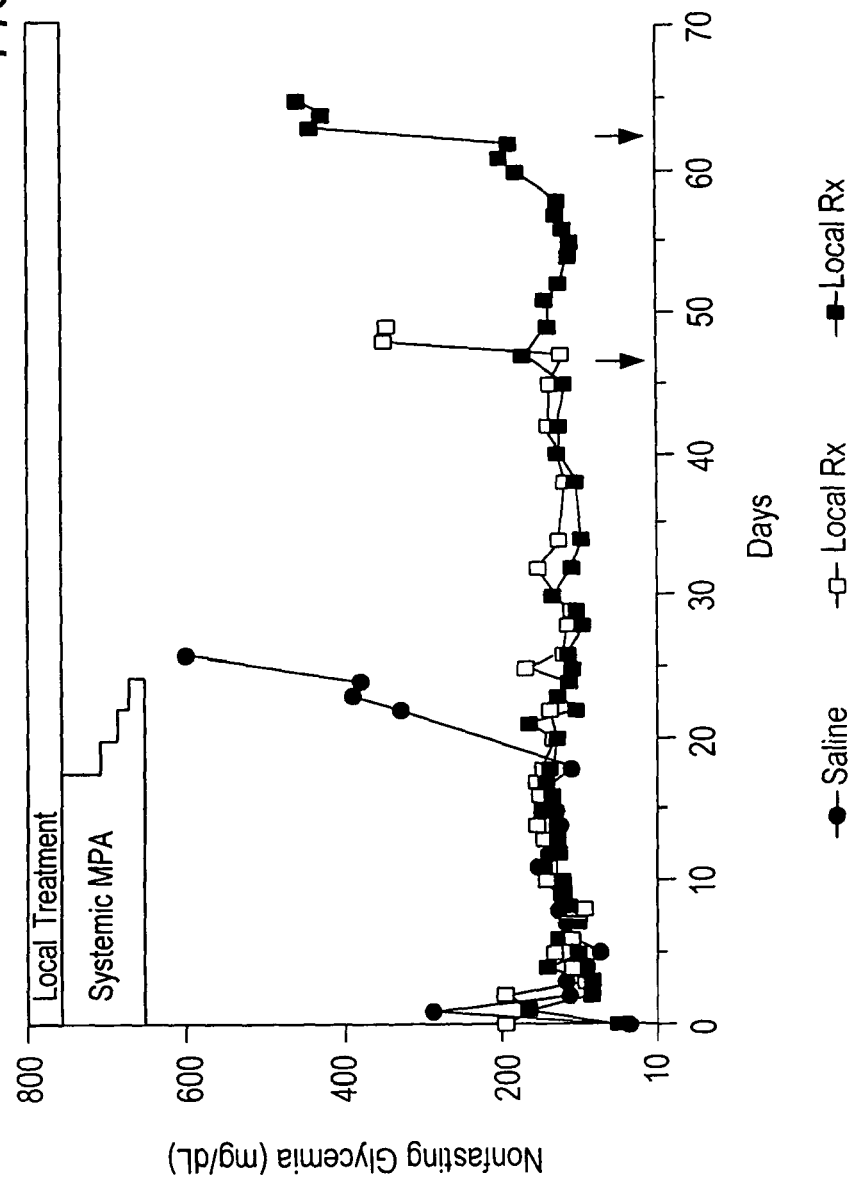
FIG. 27 shows allogeneic islet graft survival under local immunosuppression in rats. The graph summarizes the non-fasting glycemic values of a control rat (receiving local injections of saline) and of two S1P agonist-treated rats. The control animal rejected the islet allograft after completion of the weaning protocol of systemic immunosuppression (solid circles). Animals receiving daily S1P agonist injections via the injection port for localized immunosuppression at the site of islet transplantation (in the hybrid device) maintained graft function until removal of the graft-bearing device (arrows) that resulted in hyperglycemia.
Figure 28A:
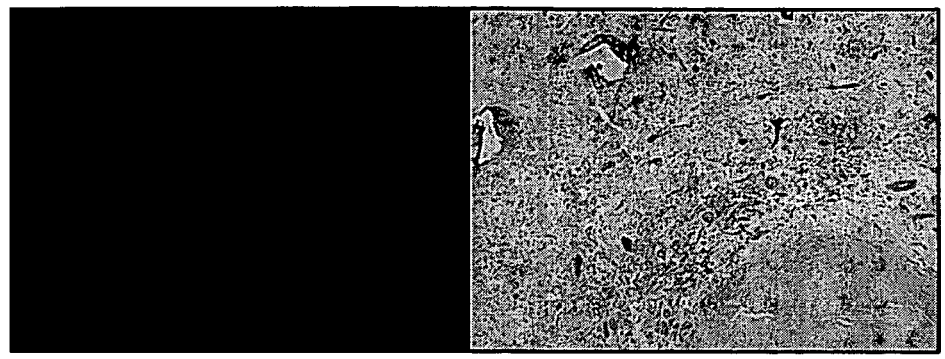
FIG. 28 shows the histopathology of allogeneic islet grafts from explanted hybrid devices of animals under local immunosuppression. The control animal rejected the islet allograft after completion of the weaning protocol of systemic immunosuppression and showed only areas of fibrosis with localized foci of mononuclear cells indicative of allograft rejection (FIG. 28A, right panel) and displayed absence of insulin-immunoreactivity by immunofluorescence microscopy (FIG. 28A, left panel). The tissue of a device explanted on day 46, more than two weeks after discontinuation of the systemic immunosuppression, showed well-preserved islet structures without infiltrating mononuclear cells within the device and only minimal presence of foci of mononuclear cells (FIG. 28B, right panel). Furthermore, islets in these sections showed intense insulin immunoreactivity (FIG. 28B, left panel) indicative of preserved functional competence.
Figure 28B:
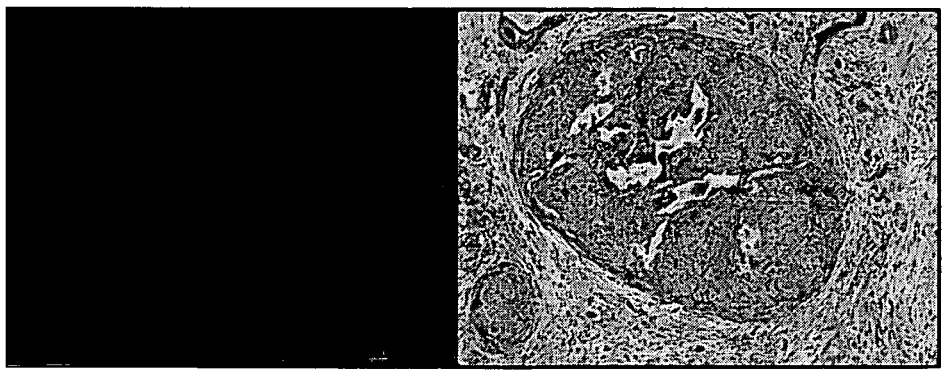

In another implementation for local immunosuppression, animals received daily injections of a S1P receptor agonist (60 uL, 50 mg/L) through a port-a-cath (Min-Ute Mouse Port, Access Technologies, Skokie, Ill.) connected to the implanted device. This approach allowed an approximate ten-fold increase in the daily dose compared to the micro-osmotic pump; nevertheless, these doses were still about 100-fold less than the systemic doses known in the arts to have immunosuppressive effects. Local immunosuppression with this approach resulted in a significant prolongation of islet graft survival up to 60 days (FIG. 27), and the obtained preliminary histological results also confirm the effectiveness of local immunosuppression alone (FIG. 28). The control animal rejected the islet allograft after completion of the weaning protocol of systemic immunosuppression and showed only areas of fibrosis with localized foci of mononuclear cells indicative of allograft rejection (FIG. 28A, right panel) and displayed absence of insulin-immunoreactivity by immunofluorescence microscopy (FIG. 28A, left panel). Animals receiving daily local immunosuppression via the injection port connected to the device maintained graft function until removal of the graft-bearing device (FIG. 27). The tissue of a device explanted on day 46, more than two weeks after discontinuation of the systemic immunosuppression, showed well-preserved islet structures without infiltrating mononuclear cells within the device and only minimal presence of foci of mononuclear cells (FIG. 28B, right panel).

Furthermore, islets in these sections showed intense insulin immunoreactivity (FIG. 28B, left panel) indicative of preserved functional competence.

EXAMPLE 6

Figure 29:
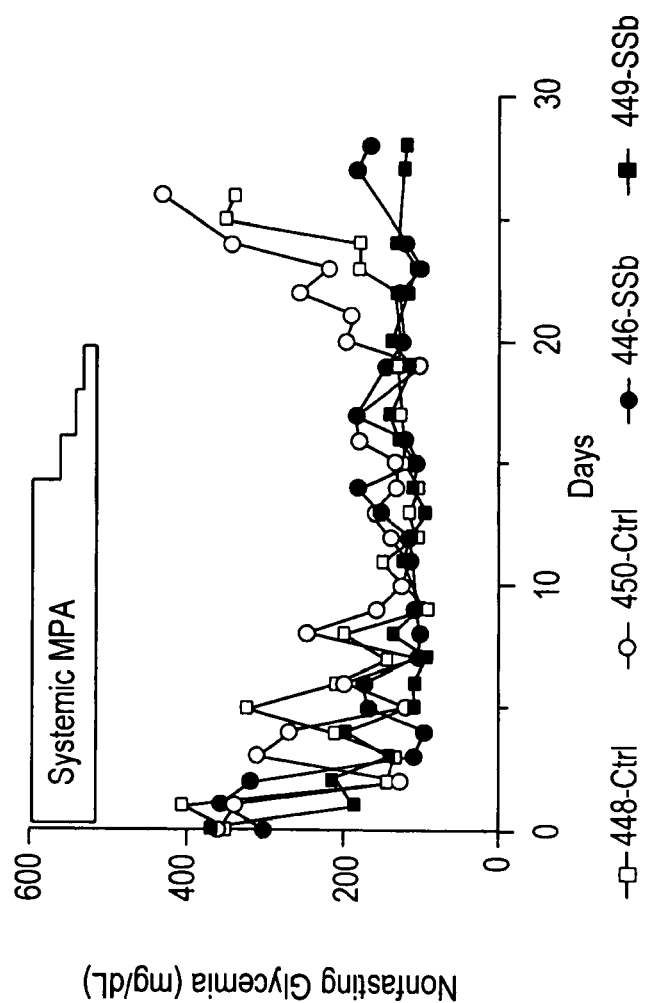
FIG. 29 shows glycemic profiles of Lewis rat recipients of allogeneic islets and sustained release soft steroid beads in hybrid devices. After the weaning protocol of systemic MPA, control animals rejected their grafts, while animals with local soft steroid beads (SSb) maintained normoglycemia for at least an additional 1-2 weeks (ongoing).

Transplant Viability in Animals Implanted with a Hybrid Device Comprising Islets of Langerhans, with Sustained Release Local Immunosuppression Chemically-diabetic Lewis rats (see above) received 7,000 IEQ of Wistar Furth islets into prevascularized hybrid devices. Immunosuppression induction consisted of a single intravenous dose of Anti Lymphocyte Serum (ALS) on day −3. Starting on the day of islet transplantation, systemic Mycophenolic Acid (20 mg/kg) was administered for at least 3 weeks. Local immunosuppression was achieved by co-transplanting sustained release PLA (polylactic acid) microspheres containing ~4% loteprednol etabonate (soft steroid beads, SSb; with an estimated 60 day release time). After the weaning protocol of systemic MPA, control animals rejected their grafts, while animals with local SSb maintained normoglycemia for at least an additional 1-2 weeks (ongoing) (FIG. 29). These data suggest that local immunosuppression attained by slow releasing beads may assist in prolonging cellular allograft survival in hybrid devices.

EXAMPLE 7

Figure 30:
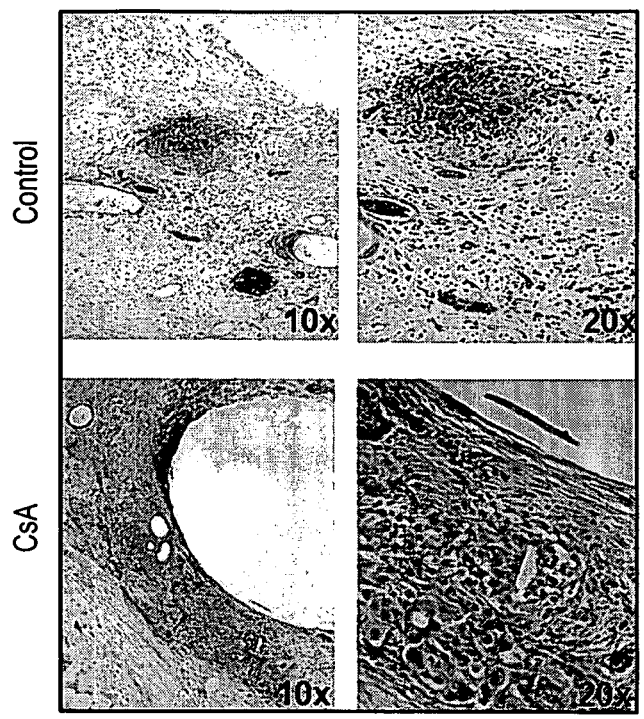
FIG. 30 shows a histopathological assessment of islet allografts in prevascularized hybrid devices in mice after co-transplantation with cyclosporin A (CsA) polymeric nanovesicles and micelles. Control explants showed islets structures severely infiltrated with mononuclear cells (upper panels), a pattern consistent with allograft rejection. Conversely, well preserved islet structures were observed in devices of islets-CsA nanocontainer co-implants (lower panels).

Histopathological Assessment of Islet Allografts in Animals Implanted with a Hybrid Device Comprising Islets of Langerhans, with Sustained Release Local Immunosuppression Six weeks after implantation of hybrid devices into C57BL/6 mice, DBA/2 donor islets were transplanted into the prevascularized devices without systemic immunosuppression. Local immunosuppression consisted of cotransplantation of Cyclosporin A (CsA) polymeric nanocontainers that allow for the slow release of the drug over a period of approximately 2 weeks. Control animals received no treatment. Devices were explanted 10 days after islet transplantation. A representative histopatological pattern of tissue from explanted devices is shown. Control explants showed islet structures severely infiltrated with mononuclear cells (FIG. 30, upper panels), a pattern consistent with allograft rejection. Conversely, well preserved islet structures were observed in devices that comprised islet-CsA nanocontainer co-implants (FIG. 30, lower panels). These data indicate that local immunosuppression may be of assistance in reducing the immune reaction to allogeneic implanted cellular grafts in hybrid devices.

EXAMPLE 8

Transplant Viability and Function in Non-Human Primates Implanted with a Hybrid Device Comprising Islets of Langerhans To assess the ability of allogeneic islets to survive in a hybrid device that has been implanted in an omental pouch site in a nonhuman primate, 2 baboons (*Papio hamadryas*) (5-6 kg) and 1 cymologus monkey (*Macaca fascicularis*) (5 kg) were rendered diabetic with streptozotocin. A hybrid device was implanted at 29-51 days prior to islet transplant in order to prevascularize the site. One day prior to islet transplant, immunosuppression was initiated. For the baboons, 10 mg/kg thymoglobulin IV on POD −1, 0, +1, and +2; 10 mg/kg mycophenolate mofetil PO BID on POD −1, POD 0 and thereafter 2.5 mg/kg BID; and 0.02 mg/kg FK506 IM BID starting on POD −1, adjusted to maintain trough levels of 4-6 ng/mL, were used. For the cynomolgus monkey, 1 mg/kg Daclizumab IV on POD −1 and 1 mg/kg IV every 2 weeks thereafter for a total of 5 doses, 0.05 mg/kg rapamycin IM BID on POD −1 and −1, 0.025 mg/kg IM BID thereafter, adjusted to maintain trough levels of 15-20 ng/mL; and 0.02 mg/kg FK506 IM BID starting on POD −1, adjusted to maintain trough levels of 4-6 ng/mL.

For each of the 2 baboons, islets from two donors were combined to achieve an islet mass of 15,000 islet equivalents (IEQ) per kg recipient body weight; for the cynomolgus monkey, a very low islet mass of 3,327 IEQ/kg was implanted from one donor. The results of in vitro glucose stimulated insulin release analyses suggested that the baboon islets were sub-optimal, but the cynomolgus monkey islets were excellent. Baboons were immunosuppressed with thymoglobulin, mycophenolate mofetil and FK506 (see above for details on dosing and timing) and the cynomolgus monkey was treated with Daclizumab, rapamycin and FK506 (see above for details on dosing and timing). Fasting and post-prandial blood glucose were measured daily and the subjects were treated with NPH and Lantus® insulin as needed.

Figure 31:
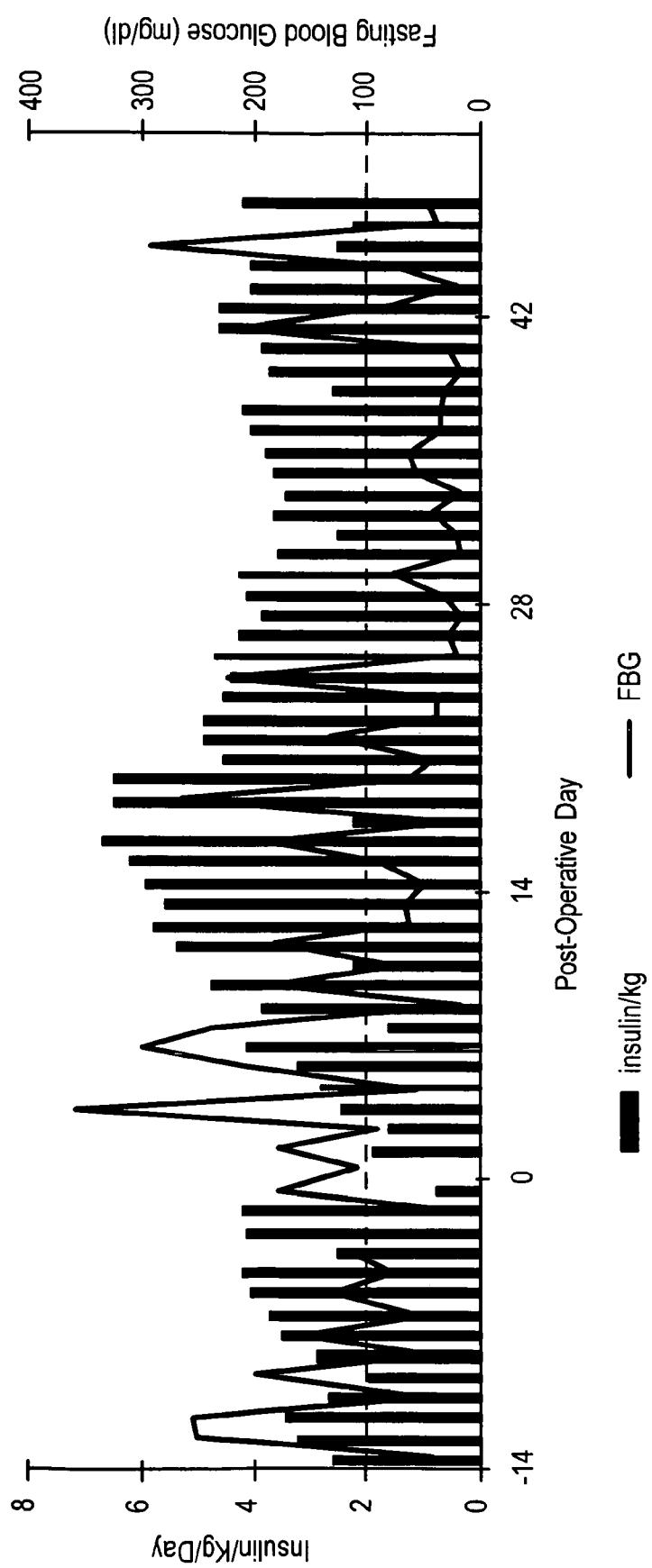
FIG. 31 shows insulin/kg and fasting blood glucose (FBG) for baboon 5P56. Daily insulin/kg requirements are shown in bars and fasting blood glucose (FBG) is shown in a solid line. A delay was observed in function, and decreased insulin requirements and lowered FBG became evident on day 20 and was maintained through post-operative day (POD) 42.
Figure 32:
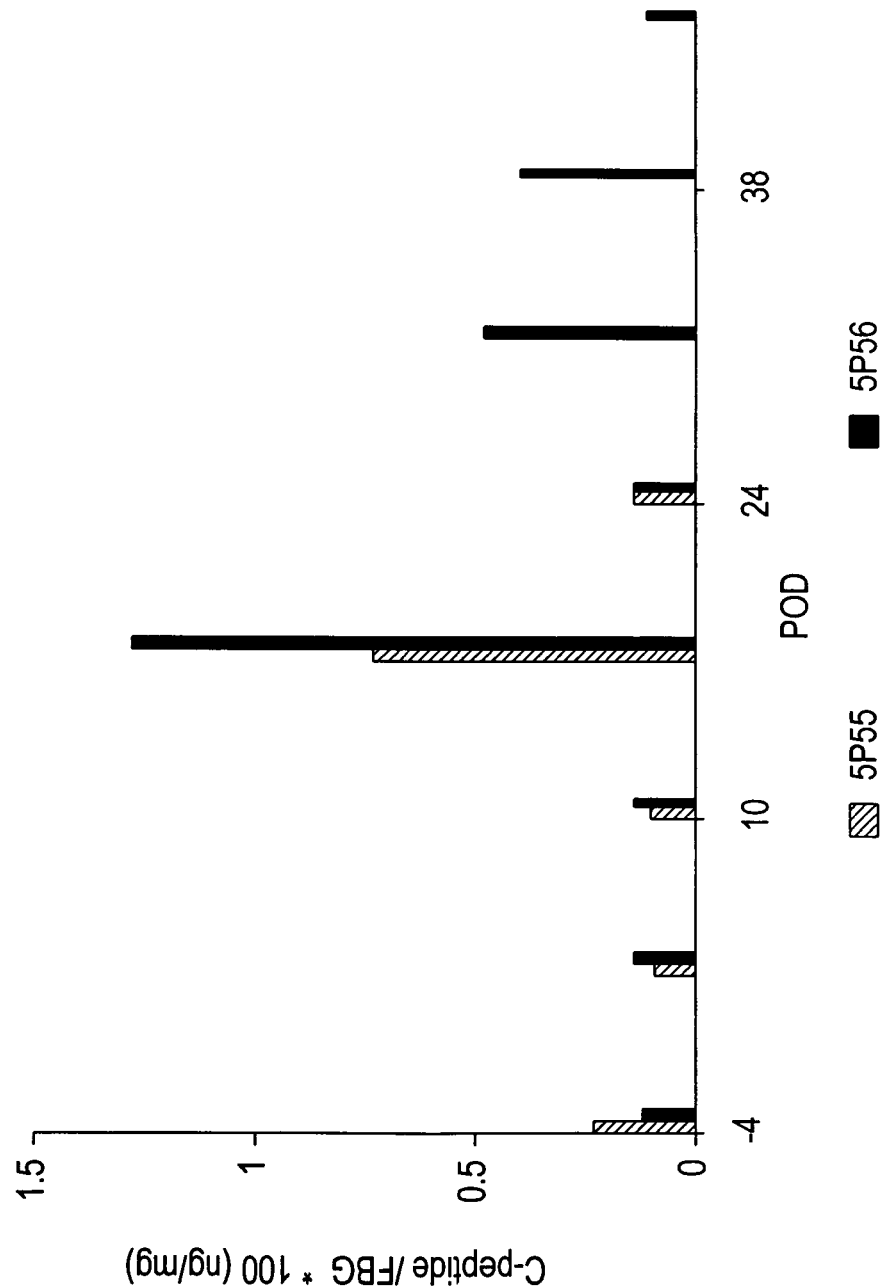
FIG. 32 shows the fasting c-peptide, corrected for FBG, for baboons 5P55 and 5P56. The highest c-peptide levels were observed on POD 17 for both animals, but 5P56 maintained positive c-peptide through the POD 38 time point.
Figure 33A:
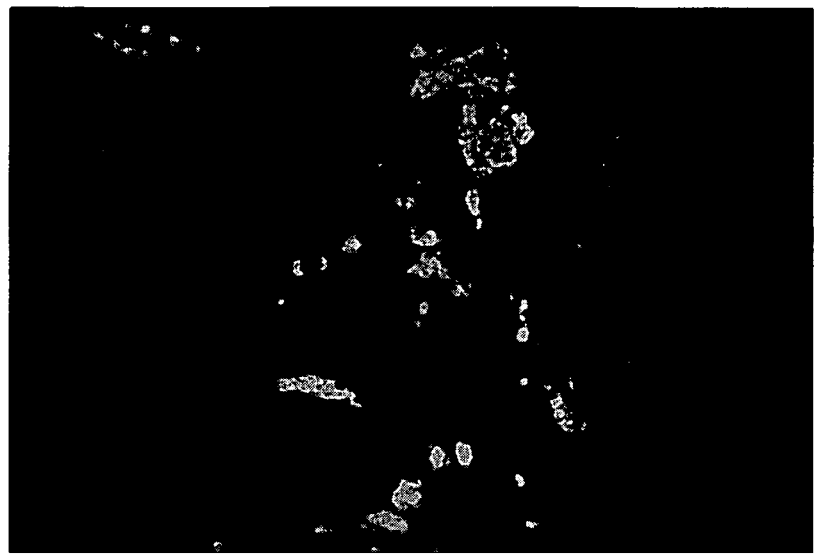
FIG. 33 shows histology results for baboon 5P55. Insulin-positive cells were clearly detected (stained green) but were low in number. Vasculature is stained red subsequent to lectin infusion in the circulation.
Figure 33B:
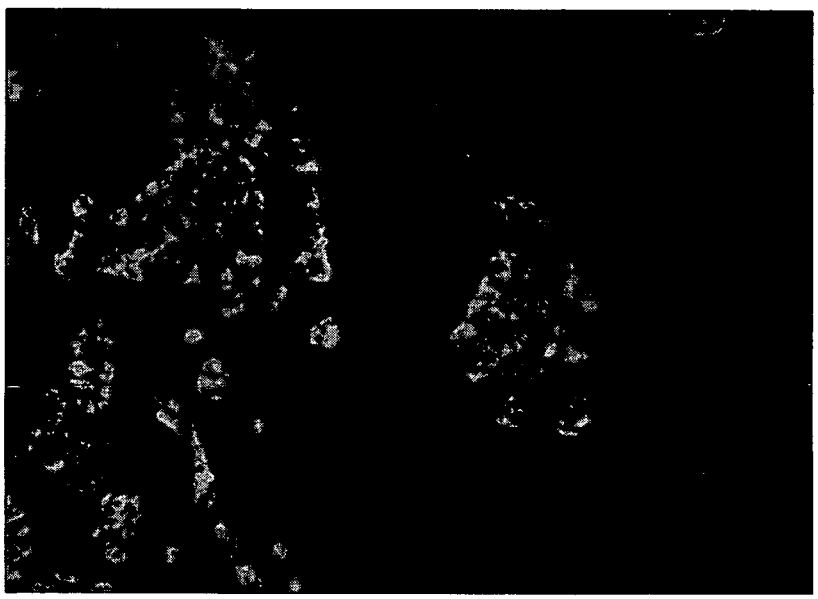

The best in vivo function was obtained for baboon 5P56 (FIG. 31). Baboon 5P56 was implanted with the hybrid device on POD –51 and underwent elective necropsy on POD 48. Daily insulin/kg requirements are shown in bars and fasting blood glucose (FBG) is shown in a solid line. Similar to our previous observations utilizing the omental pouch site for islet implant without a device, there was a delay in function, and decreased insulin requirements and lowered FBG became evident on day 20 and was maintained through postoperative day (POD) 42. FIG. 32 shows the fasting c-peptide, corrected for FBG, for the 2 baboons. The highest c-peptide levels were observed for the POD 17 for both animals, but 5P56 maintained positive c-peptide through the POD 38 time point. Based on extensive experience, it appeared that both animals experienced rejection, and this was supported by the histology results (FIG. 33), in which insulin positive cells were clearly detected (stained green) but were low in number. This was the first time we had used the thymoglobulin/MMF/FK506 combination for immune suppression, and it was clearly not effective after the lymphocytes began to recover from the depletion induced by thymoglobulin.

Figure 34A:
FIG. 34 shows H&E staning of explant tissue from cynomolgus monkey CW3G. At the time of explant, well-preserved insulin-positive tissue (stained brown) was clearly observed.
Figure 34B:
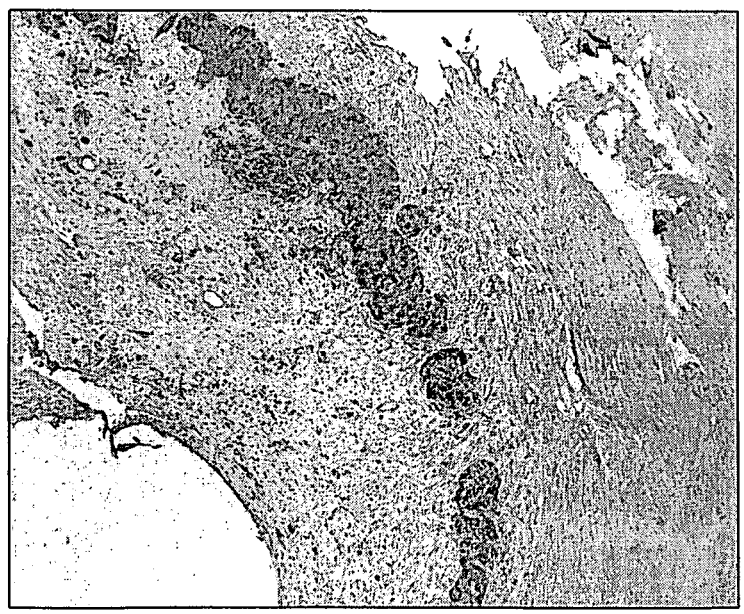

Due to the extremely low islet mass, there was minimal evidence of function for the cynomolgus monkey, which was immunosuppressed with a protocol that we have proven is effective in the first months post-transplant in nonhuman primates. At the time of explant, however, well-preserved insulin positive tissue (stained brown) was clearly observed (FIG. 34). Unlike the baboons that had undergone a rejection response and had only sporadic small clusters of insulin positive cells, the observed islet tissue in the cynomolgus monkey appeared normal.

This preliminary data clearly demonstrates that islet tissue can survive in a device placed within an omental pouch site in a nohuman primate, strongly suggesting that implantation of an adequate mass of functional islets that are protected with effective immune suppression (whether local or systemic) is possible.

EXAMPLE 9

Encapsulation and Transplantation of Islets of Langerhans

A device of the invention, containing a plunger in the adjacent space, is manually placed into the intraperitoneal cavity of the subject in such a manner that the port is externally accessible. Following the implantation procedure, the surgical site is closed around the port. The device remains in the site for two weeks, allowing for vascularization of the area surrounding the device. During this time, the port is connected to an external or externally accessible pump that delivers pro-vascularization factors, including VEGF, through the distribution conduits, aiding the vascularization process.

When two weeks have passed, islets of Langerhans are isolated from the pancreas of a human cadaver donor. The pancreas is perfused with cold HBSS containing collagenase. The distended pancreas is digested with the cold solution for 10 minutes, warmed to the range of 28-32° C., then submerged in collagenase solution, which is subsequently heated to 34° C. The pancreas is then shaken manually or by machine for about 10-15 minutes. The digested tissue is diluted and collected with cold dilution solution containing HSA to neutralize the effect of the enzyme. The tissue is filtered, centrifuged at a low speed and washed. The islet cells are separated on a Ficoll gradient with a COBE automatic cell separator, then incubated in Miami Media #1A (see, e.g., Fraker et al., *Cell Transplant.* 13(5):497-502 (2004)) for 24-48 hours prior to transplant.

Islets are then nanocoated. Isolated islets are suspended in medium containing 10% fetal bovine serum, then pelleted by centrifugation for 3 minutes. The pellet is then mixed with 2% alginate at the desired loading concentration (v/v). The alginate/islet suspension is then extruded via a 20-gauge needle into a 1.1% $CaCl_2$ solution; the droplet size is controlled by parallel airflow. Capsules are then rinsed with DPBS and placed in a spinner flask, fed with fully supplemented RPMI medium, and positioned within a 37° C. humidified incubator.

The pump is disconnected from the port of the device. A partial incision is made to expose the plunger access end, and the plunger is removed from the device. A small catheter connected to a syringe is used to deliver the nanocoated islets to the vascularized space previously occupied by the plunger. The surgical site is closed around the port, and the external or externally accessible pump is reconnected to the port. Immunomodulatory and pro-survival factors are pumped through the distribution conduits to the nanocoated islets.

EXAMPLE 10

Regulation of Glucose Levels in Animals Implanted with a Hybrid Device Comprising Non-Encapsulated Islets Animal subjects (Rhesus monkeys) are chemically rendered diabetic (e.g., through administration of streptozotocin). The animal subjects are then implanted with a device of the invention comprising a plunger, as in Example 9, and allowed to recover for two weeks during the vascularization phase.

Islets are isolated as described in Example 9. A partial incision is made and the plunger is removed from the device, as in Example 9. Using a small catheter connected to a syringe, the isolated islets are deposited in the devices of half of the animal subjects. No islets are deposited in the devices of the other half of the animal subjects. After transplantation, the animals' blood glucose levels are monitored daily. It is expected that the animals implanted with islet cells will demonstrate greater regulation of blood glucose levels than animals not implanted with islet cells.

EXAMPLE 11

Regulation of Glucose Levels in Animals Implanted with a Hybrid Device Comprising Microencapsulated Islets Animal subjects (Rhesus monkeys) are rendered diabetic as in Example 10. The animal subjects are then implanted with a device of the invention comprising a plunger, as in Example 9, and allowed to recover for two weeks during the vascularization phase.

Islet cells are isolated as in Example 9. Half are not encapsulated, and half are microencapsulated as follows. Islets are suspended in 1.4% sodium alginate and placed in a droplet generator. The islet-containing droplets generated are gelled in a funnel containing 1.1% $CaCl_2$. The resulting microcapsules are washed with normal saline (NS), incubated with 0.05% poly-L-lysine, washed again with NS, incubated with alginate, and washed a final time with NS.

A partial incision is made and the plunger is removed from the device, as in Example 9. Using a small catheter connected to a syringe, half of the animal subjects receive microencapsulated islets in the device. The other half receive non-encapsulated islets in the device. After transplantation, the animals' blood glucose levels are monitored daily. Animals implanted with the device comprising microencapsulated islets will demonstrate greater and more long-term regulation of blood glucose levels than animals implanted with the device comprising non-encapsulated islets.

EXAMPLE 12

Regulation of Glucose Levels in Animals Implanted with a Hybrid Device Comprising Nanocoated Islets Animal subjects (Rhesus monkeys) are rendered diabetic as in Example 10. Three-quarters of the animal subjects are implanted with a device of the invention comprising a plunger, as in Example 9, and allowed to recover for two weeks during the vascularization phase.

Islets are isolated as in Example 9. Half of the islets are nanocoated as in Example 9, while the other half remain non-nanocoated.

A partial incision is made and the plunger is removed from the device for each of the device-implanted animal subjects, as in Example 9. Using a small catheter connected to a syringe, nanocoated islets are deposited in one third of the devices, non-nanocoated islets are deposited in one third of the devices, and an identical volume of solution with no islets is deposited in one third of the devices. The remaining quarter of the animal subjects are intraperitoneally injected with nanocoated islets alone, without the device.

After transplantation, the animals' blood glucose levels are monitored daily. It is expected that the animals implanted with the islets or islet cell-containing devices are expected to demonstrate greater regulation of blood glucose levels than the animals implanted with devices lacking islet cells. It is further expected that regulation of glucose levels will be greater and more long-term in animals implanted with the device comprising nanocoated islets than animals implanted with the device comprising non-nanocoated islets or nanocoated islets alone.

EXAMPLE 13

Regulation of Glucose Levels in Animals Implanted with Microencapsulated or Nanocoated Islets Animal subjects (Rhesus monkeys) are rendered diabetic as in Example 10. The animal subjects are then implanted with a device of the invention comprising a plunger, as in Example 9, and allowed to recover for two weeks during the vascularization phase.

Islet cells are isolated as in Example 9, then one third are nanocoated as in Example 9, one third are microencapsulated as in Example 11, and one third are not encapsulated.

A partial incision is made and the plunger is removed from the device, as in Example 9. Using a small catheter connected to a syringe, one third of the animal subjects receive nanocoated islets in the device; one third receive microencapsulated islets; and one third receive non-encapsulated islets. After transplantation, the animals' blood glucose levels are monitored daily. Animals implanted with nanocoated islets are expected to demonstrate greater and more long-term regulation of blood glucose levels than the animals implanted with microencapsulated islets or non-nanocoated islets.

EXAMPLE 14

Regulation of Glucose Levels in Animals Implanted with or without a Hybrid Device, Comprising Non-Encapsulated, Microencapsulated, or Nanocoated Islets, with or without Immunosuppression Animal subjects (Rhesus monkeys) are rendered diabetic as in Example 10. Three-quarters of the animal subjects are implanted with a device of the invention comprising a plunger, as in Example 9, and allowed to recover for two weeks during the vascularization phase.

Islets are isolated as in Example 9. One third are microencapsulated as in Example 11, one third are nanocoated as in Example 9, and one third are non-encapsulated.

A partial incision is made and the plunger is removed from the device for each of the device-implanted animal subjects, as in Example 9. Using a small catheter connected to a syringe, nanocoated islets are deposited in one third of the devices, microencapsulated islets are deposited in one third of the devices, and non-encapsulated islets are deposited in one third of the devices.

The animals are separated into eight groups:
1. no encapsulation, no device, no immunosuppression
2. no encapsulation, no device, immunosuppression
3. no encapsulation, device, no immunosuppression
4. no encapsulation, device, immunosuppression
5. microencapsulation, device, no immunosuppression
6. microencapsulation, device, immunosuppression
7. nanocoating, device, no immunosuppression
8. nanocoating, device, immunosuppression Immunosuppression is delivered in the form of sirolimus and tacrolimus.

After transplantation, the animals' blood glucose levels are monitored daily. It is expected that the animals implanted with the nanocoated islets will demonstrate greater regulation of blood glucose levels than the animals implanted with microencapsulated or non-encapsulated islets. It is further expected that regulation of glucose levels will be greater and more long-term in animals implanted with the device comprising nanocoated islets than animals implanted with the device comprising non-nanocoated islets or nanocoated islets alone. It is further expected that, in non-immunosuppressed animals regulation of glucose levels will be greater and more long-term in animals implanted with nanocoated islets than in animals implanted with microencapsulated islets.

EXAMPLE 15

Regulation of Glucose Levels in Human Patients Implanted with a Hybrid Device Comprising Nanocoated Human Islets Human patients with diabetes are implanted with a device of the invention comprising islets that have been isolated and nanocoated as in Example 9. Preferably, the islets are allogeneic or syngeneic.

After transplantation, the patients' blood glucose levels are monitored daily. It is expected that regulation of blood glucose levels will improve upon implantation of the device.

EXAMPLE 16

Regulation of Glucose Levels in Human Patients Implanted with a Hybrid Device Comprising Nanocoated Porcine Islets Human patients with diabetes are implanted with a device of the invention, comprising a plunger in the adjacent space, as in Example 9. The patients then recover for two weeks during the vascularization phase.

Islets are isolated essentially as described in U.S. patent application Ser. No. 10/761,180 (published as U.S. Patent Publication No.: US 2004/0195710). The pancreas of an anesthetized pig is perfused with University of Wisconsin solution (Dupont) and then removed by pancreatectomy. The pancreatic ducts are distended with HBSS containing 1 mM Trolox (an antioxidant), 1.5 mg/ml collagenase and 10,000 units DNAse 1. The distended pancreas is digested on ice for 30 minutes, then incubated at 37° C. for 20 minutes. The pancreas is then manually shaken for one minute. The digested tissue is mesh-filtered and centrifuged at a low speed in CMRL-based culture medium. The islet cells are separated on a Ficoll gradient with a COBE automatic cell separator, then incubated for 18-24 hours in CMRL-based medium containing 5 cc of a mixture of streptomycin/penicillin (per 100 ml culture medium), 10 mM dimethylthiourea, 5 mM citiolone, 2 mM L-NMMA, and 10 mM GSH.

A partial incision is made and the plunger is removed from the device, as in Example 9. Using a small catheter connected to a syringe, the isolated, nancoated islets are deposited in the devices and the surgical openings are closed.

After transplantation, the patients' blood glucose levels are monitored daily. It is expected that regulation of blood glucose levels will improve upon implantation of the device. It is further expected that systemic or localized immunosuppression of the patient can be reduced by thus using the methods and devices of this invention.

EXAMPLE 17

Improvement of Cognitive Function in Alzheimer's Disease Patients Implanted with a Hybrid Device Comprising NGF-Secreting Cells Delivery of nerve growth factor (NGF) to the CNS is believed to improve cognitive function in Alzheimer's disease patients. Implantation of NGF-secreting cells may provide long-term therapeutic benefit. It is expected that cells that have been nanocoated and loaded into a port-containing device through the methods of this invention will survive longer and be of greater therapeutic benefit than cells implanted by previously known methods BHK cells releasing human NGF are nanocoated as in Example 9. The nanocoated cells are then loaded through a catheter into a device of the invention. The device is stereotoxically placed in a selected neocortical/hippocampal region of the subject and the surgical opening is closed around the port of the device. The port is connected to an external or externally accessible pump. Immunoregulatory and/or pro-survival factors are pumped through the port to distribution conduits that deliver said factors to the nanocoated cells, enhancing survival of the implanted cells. After three to four weeks, patients are assessed for improvement of cognitive function through tests such as: (1) mini-mental state examination (Folstein et al., *J Psychiatr Res* 12:189-198 (1975)); (2) face recognition exam (Backman et al., *Psychol Aging* 6:489-492 (1991)); (3) spatial memory with immediate and delayed (30 minute) testing. It is expected that performance on such tests will improve upon implantation of the device.

All publications and patent applications cited in this specification are incorporated herein by reference as if each individual publication or patent application were specifically and individually indicated to be incorporated by reference.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims. For example, in an alternative configuration, as mentioned above, the device could be implanted without the plunger, already containing the biological material, without providing for a first phase of vascularization between mesh and plunger, but using the "sprinkler system" to feed the implanted biological material with, for example, nutrients and growth factors, while favoring re-vascularization through the delivery of factors such as angiogenic factors.

What is claimed is:

1. A device for receiving implanted nanoencapsulated biological material comprising one or more cell types or tissues, wherein said device comprises:
  a) a mechanoprotective surface defining an adjacent space for receiving the implanted biological material, wherein said mechanoprotective surface has a porosity which permits vasculature to reach said adjacent space; and
  b) at least one agent formulated or encapsulated to provide slow/sustained release delivery to the implanted biological material, wherein said agent is or comprises at least one factor selected from the group consisting of an oxygen generating product, an oxygen releasing product, an oxygen transport enhancing product, and an immunosuppressive agent.

2. The device of claim 1, wherein the agent further comprises one or more of: a vascularization agent; a cytoprotective agent; an antiapoptotic agent; a tolerance inducing agent; an anti-inflammatory factor; an immunoregulatory agent; and a growth factor.

3. The device of claim 1, wherein the agent is or comprises dexamethasone.

4. The device of claim 1, wherein the biological material comprises pancreatic islet cells.

5. The device of claim 1, wherein the biological material is implanted with at least one type of helper cell.

6. The device of claim 5, wherein the at least one type of helper cell is selected from mesenchymal cells and regulatory T cells.

7. The device of claim 1, wherein the adjacent space comprises a biocompatible matrix material that comprises at least one factor that aids in the establishment, maintenance, or long term survival or function of the biological material.

8. The device of claim 7, wherein the biocompatible matrix material comprises at least one factor selected from the group consisting of an oxygen generating product, an oxygen releasing product, an oxygen transport enhancing product, and an immunosuppressive agent.

9. The device of claim 1, wherein said agent comprises at least one oxygen generating, releasing, or transport enhancing product in combination with at least one immunosuppressive agent.

10. The device of claim 1, wherein the agent is or comprises a perfluorocarbon (PFC).

11. The device of claim 1, wherein the device is a sponge-like mesh element.

12. The device of claim 1, wherein said mechanoprotective surface is a macrostructure scaffold.

13. A method of implanting biological material comprising one or more cell types or tissues in a patient, comprising the step of implanting into the patient a device as in claim 1.

14. The method of claim 13, wherein the implant location is intraomental, subcutaneous, intraperitoneal, intramuscular, or renal subcapsular.

15. A device for receiving implanted biological material comprising one or more cell types or tissues, wherein said device comprises:
   a) a mechanoprotective surface defining an adjacent space for receiving the implanted biological material, wherein said mechanoprotective surface has a porosity which permits vasculature to reach said adjacent space; and
   b) at least one agent formulated or encapsulated to provide slow/sustained release delivery to the implanted biological material, wherein said agent is or comprises oATP.

16. A method of implanting biological material comprising one or more cell types or tissues in a patient, comprising the steps of:
   (1) implanting into the patient a device comprising: a) a mechanoprotective surface defining an adjacent space for receiving the biological material, wherein said mechanoprotective surface has a porosity which permits vasculature to reach said adjacent space, b) at least one agent formulated or encapsulated to provide slow/sustained release delivery to the implanted biological material, wherein said agent comprises at least one factor selected from the group consisting of an oxygen generating product, an oxygen releasing product, an oxygen transport enhancing product, and an immunosuppressive agent, and c) a plunger element in the adjacent space;
   (2) waiting for a period of time sufficient for ingrowth of vascular tissue into the adjacent space; and,
   (3) removing the plunger element and depositing the biological material into the space vacated by the plunger element, and providing slow/sustained release delivery of said at least one agent to the biological material.

17. The method of claim 16, wherein the adjacent space comprises a biocompatible matrix material that comprises at least one factor that aids in the establishment, maintenance, or long term survival or function of the biological material.

18. The method of claim 16, wherein the implant location is intraomental, subcutaneous, intraperitoneal, intramuscular, or renal subcapsular.

19. A device for receiving implanted biological material comprising one or more cell types or tissues, wherein said device comprises:
   a) a mechanoprotective surface defining an adjacent space for receiving the implanted biological material, wherein said mechanoprotective surface has a porosity which permits vasculature to reach said adjacent space; and
   b) at least one agent formulated or encapsulated to provide slow/sustained release delivery to the implanted biological material, wherein said agent is or comprises encapsulated peroxide.

* * * * *